(12) United States Patent
Wei et al.

(10) Patent No.: US 6,569,994 B1
(45) Date of Patent: May 27, 2003

(54) HUMAN BLUE-LIGHT PHOTORECEPTOR HCRY2

(75) Inventors: Ying-Fei Wei, Darnestown, MD (US); Steven M. Ruben, Olney, MD (US); Aziz Sancar, Chapel Hill, NC (US); Shiao-Wen D. Hsu, Durham, NC (US); Aleksey G. Kazantsev, Chapel Hill, NC (US)

(73) Assignees: Human Genome Sciences, Inc., Rockville, MD (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/105,254

(22) Filed: Jun. 26, 1998

Related U.S. Application Data

(62) Division of application No. 08/964,268, filed on Nov. 4, 1997, now Pat. No. 6,114,503.
(60) Provisional application No. 60/030,189, filed on Nov. 4, 1996.

(51) Int. Cl.$^7$ .......................... C07K 17/00; C12N 9/00; C12P 21/06; C12Q 1/68; C07H 21/04
(52) U.S. Cl. .................. 530/350; 435/183; 435/69.1; 435/320.1; 435/325; 435/252.3; 435/6; 536/23.1
(58) Field of Search .......................... 435/183, 6, 69.1, 435/320.1, 325, 252.3; 530/350, 300; 536/23.1

(56) References Cited

FOREIGN PATENT DOCUMENTS

WO        WO 96/01897        1/1996

OTHER PUBLICATIONS

Griffin et al., Science 286:768–771, 1999.*
Van der Horst et al., Nature 398:627–630, 1999.*
Kume et al., Cell 98:193–205, 1999.*
Bork, Genome Research, 10:348–400, 2000.*
Broun et al., Science 282:1315–1317, 1998.*
Van de Loo et al., Proc. Natl. Acad. Sci. 92:6743–6747, 1995.*
Hillier, L. et al., GenBank Database, Accession No. H21100, Jul. 1995.*
Kloesgen, R. et al., GenBank Database, Accession No. P04713, Aug. 1987.*
Todo, T. et al., Science, vol. 272, pp. 109–112, Apr. 5, 1996.*
Adams, M.D. et al., "Complementary DNA Sequencing: Expressed Sequence Tags and Human Genome Project," Science 252:1651–1656 (1991).
Adams, M.D. et al., "Sequence identification of 2,375 human brain genes," Nature 355:632–634 (1992).
Adams, M.D. et al., "Initial assessment of human gene diversity and expression patterns based upon 83 million nucleotides of cDNA sequence," Nature 377:3–17 (Sep. 1995).

Ahmad, M. and A.R. Cashmore, "HY4 gene of *A. thaliana* encodes a protein with characteristics of a blue–light photoreceptor," Nature 366:162–166 (1993).
Ahmad, M. and A.R. Cashmore, "Seeing blue: the discovery of cryptochrome," Plant Mol. Biol. 30:851–861 (Mar. 1996).
Batschauer, A., "A plant gene for photolyase: an enzyme catalyzing the repair of UV–light–induced DNA damage," Plant J. 4(4):705–709 (1993).
Dunlap, J.C., "Genetic Analysis of Circadian Clocks," Annu. Rev. Physiol. 55:683–728 (1993).
Hohl, N. et al., "Altered Pterin Patterns in Photobehavioral Mutants of *Phycomyces blakesleeanus*," Photochem. & Photobiol. 55(2):239–245 (1992).
Kato, T., Jr. et al., "Cloning of a marsupial DNA photolyase gene and the lack of related nucleotide sequences in placental mammals," Nucl. Acids Res. 22(20):4119–4124 (1994).
Kim, S.–T. et al., "Characterization of (6–4) Photoproduct DNA Photolyase," J. Biol. Chem. 269(11):8535–8540 (1994).
Kim, S.–T. et al., "Purification and Partial Characterization of (6–4) Photoproduct DNA Photolyase from *Xenopus laevis*," Photochem. & Photobiol. 63(3):292–295 (Mar. 1996).
Kim, S.–T., et al. "Purification and characterization of *Drosophila melanogaster* photolyase," Mut. Res. 363:97–104 (Jun. 1996).
Ley, R.D., "Photoreactivation in humans," Proc. Natl. Acad. Sci. USA 90:4337 (1993).
Li, Y.F. et al., "Evidence for lack of DNA photoreactivating enzyme in humans," Proc. Natl. Acad. Sci. USA 90:4389–4393 (1993).
Lin, C. et al., "Association of Flavin Adenine Dinucleotide with the Arabidopsis Blue Light Receptor CRY1," Science 269:968–970 (Aug. 1995).
Lin, C. et al., "Expression of an Arabidopsis cryptochrome gene in transgenic tobacco results in hypersensitivity to blue, UV–A, and green light," Proc. Natl. Acad. Sci. USA 92:8423–8427 (Aug. 1995).
Malhotra, K. et al., "Putative Blue–Light Photoreceptors from *Arabidopsis thaliana* and *Sinapis alba* with a High Degree of Sequence Homology to DNA Photolyase Contain the Two Photolyase Cofactors but Lack DNA Repair Activity," Biochem. 34:6892–6899 (May 1995).
Ninnemann, H., "Some Aspects of Blue Light Research During the Last Decade," Photochem. & Photobiol. 61(1):22–31 (Jan. 1995).

(List continued on next page.)

Primary Examiner—Rebecca E. Prouty
Assistant Examiner—Delia Ramirez
(74) Attorney, Agent, or Firm—Human Genome Sciences, Inc.

(57) ABSTRACT

The present invention relates to a novel member of the blue-light photoreceptor family of receptors. In particular, isolated nucleic acid molecules are provided encoding the human hCRY2 receptor. hCRY2 polypeptides are also provided as are vectors, host cells, antibodies, and recombinant methods for producing the same.

13 Claims, 12 Drawing Sheets

OTHER PUBLICATIONS

Sancar, G.B., "DNA photolyases: Physical properties, action mechanism, and roles in dark repair," *Mut. Res.* 236:147–160 (1990).

Short, T.W. and W.R. Briggs, "The Transduction of Blue Light Signals in Higher Plants," *Annu. Rev. Plant Physiol. & Plant Mol. Biol.* 45:143–171 (1994).

Small, G.D. et al., "Characterization of a *Chlamydomonas reinhardtii* gene encoding a protein of the DNA photolyase/blue light photoreceptor family," *Plant Mol. Biol.* 28:443–454 (Jun. 1995).

Sutherland, B.M. and P.V. Bennett, "Human white blood cells contain cyclobutyl pyrimidine dimer photolyase," *Proc. Natl. Acad. Sci. USA* 92:9732–9736 (Oct. 1995).

Todo, T. et al., "A new photoreactivating enzyme that specifically repairs ultraviolet light–induced (6–4)photoproducts," *Nature* 361:371–374 (1993).

Todo, T. et al., "Similarity Among the Drosophila (6–4)Photolyase, a Human Photolyase Homolog, and the DNA Photolyase–Blue–Light Photoreceptor Family," *Science* 272:109–112 (Apr. 1996).

Yasui, A. et al., "A new class of DNA photolyases present in various organisms including aplacental mammals," *EMBO J.* 13(24):6143–6151 (1994).

Genbank report, Accession No. AA297444, submitted by Adams, M.D. et al. (Apr. 1997).

Genbank report, Accession No. AA338421, submitted by Adams, M.D. et al. (Apr. 1997).

Hsu, D.S. et al., "Putative Human Blue–Light Photoreceptors hCRY1 and hCRY2 Are Flavoproteins," *Biochem.* 35:13871–13877 (Nov. 1996).

Van der Spek, P.J. et al., "Cloning, Tissue Expression, and Mapping of a Human Photolyase Homolog with Similarity to Plant Blue–Light Receptors," *Genomics* 37:177–182 (Oct. 1996).

EMBL Sequence Database, Accession No. AA297444, from Adams, M.D. et al. (Apr. 1997).

EMBL Sequence Database, Accession No. AA338421, from Adams, M.D. et al. (Apr. 1997).

EMBL Sequence Database, Accession No. AA076014, from Hillier, L. et al. (Oct. 1996).

EMBL Sequence Database, Accession No. AA461357, from Hillier, L. et al. (Jun. 1997).

EMBL Sequence Database, Accession No. AA426472, from Hillier, L. et al. (May 1997).

EMBL Sequence Database, Accession No. AA436238, from Hillier, L. et al. (Jun. 1997).

NCBI Entrez, GenBank Report, Accession No. 221657, from Auffray, C. et al. (1993).

NCBI Entrez, GenBank Report, Accession No. Z44457, from Auffray, C. et al. (1994).

NCBI Entrez, GenBank Report, Accession No. R19031, from Hillier, L. et al. (Apr. 1995).

NCBI Entrez, GenBank Report, Accession No. R73046, from Hillier, L. et al. (Jun. 1995).

NCBI Entrez, GenBank Report, Accession No. H18143, from Hillier, L. et al. (Jun. 1995).

NCBI Entrez, GenBank Report, Accession No. H43416, from Hillier, L. et al. (Jul. 1995).

NCBI Entrez, GenBank Report, Accession No. H46954, from Hillier, L. et al. (Jul. 1995).

NCBI Entrez, GenBank Report, Accession No. T33810, from Adams, M.D. et al. (Sep. 1995).

NCBI Entrez, GenBank Report, Accession No. H50432, from Hillier, L. et al. (Sep. 1995).

NCBI Entrez, GenBank Report, Accession No. W07804, from Hillier, L. et al. (Apr. 1996).

NCBI Entrez, GenBank Report, Accession No. W22305, from Macke, J. et al. (May 1996).

NCBI Entrez, GenBank Report, Accession No. W26687, from Macke, J. et al. (May 1996).

NCBI Entrez, GenBank Report, Accession No. W52891, from Hillier, L. et al. (May 1996).

NCBI Entrez, GenBank Report, Accession No. W70498, from Marra, M. et al. (Jun. 1996).

NCBI Entrez, GenBank Report, Accession No. W32115, from Hillier, L. et al. (Oct. 1996).

NCBI Entrez, GenBank Report, Accession No. AA271087, from Marra, M. et al. (Mar. 1997).

NCBI Entrez, GenBank Report, Accession No. AA317777, from Adams, M.D. et al. (Apr. 1997).

NCBI Entrez, GenBank Report, Accession No. AA356081, from Adams, M.D. et al. (Apr. 1997).

NCBI Entrez, GenBank Report, Accession No. AA461357, from Hillier, L. et al. (Jun. 1997).

NCBI Entrez, GenBank Report, Accession No. AA553227, from Marra, M. et al. (Aug. 1997).

NCBI Entrez, GenBank Report, Accession No. AA672313, from Marra, M. et al. (Nov. 1997).

NCBI Entrez, GenBank Report, Accession No. AA076014, from Hillier, L. et al. (Dec. 1997).

International Search Report for International Application No. PCT/US97/20920, mailed Apr. 7, 1998.

* cited by examiner

```
                          -30                          -10
        GGCCACGCGTCGACTAGTACGGGGGGGGGGGGGGGGCATTCTGGACAGTCATGGCGGC
                                                              M  A  A
          10              30              50
        AACTGTGGCAACGGCGGCAGCTGTGGCCCCGGCGCCAGCGCCCGGCACGGACAGCGCCTC
         T  V  A  T  A  A  A  V  A  P  A  P  A  P  G  T  D  S  A  S
         70              90             110

TTCGGTGCACTGGTTCCGCAAAGGGCTGCGACTCCACGACAACCCGGCGTTGCTGGCGGC
         S  V  H  W  F  R  K  G  L  R  L  H  D  N  P  A  L  L  A  A
        130             150             170

CGTGCGCGGGGCGCGCTGCGTGCGCTGCGTTTACATTCTCGACCCGTGGTTCGCGGCCTC
         V  R  G  A  R  C  V  R  C  V  Y  I  L  D  P  W  F  A  A  S
        190             210             230

CTCCTCAGTCGGGATCAACCGATGGAGGTTCCTACTTCAGTCTCTGGAAGATTTGGACAC
         S  S  V  G  I  N  R  W  R  F  L  L  Q  S  L  E  D  L  D  T
        250             270             290

AAGTTTAAGGAAACTGAACTCCCGCCTGTTTGTAGTCCGGGGACAGCCAGCCGACGTGTT
         S  L  R  K  L  N  S  R  L  F  V  V  R  G  Q  P  A  D  V  F
        310             330             350

CCCAAGGCTGTTCAAGGAATGGGGAGTGACCCGCTTGACCTTTGAACATGACTCTGAACC
         P  R  L  F  K  E  W  G  V  T  R  L  T  F  E  H  D  S  E  P
        370             390             410

CTTTGGGAAAGAACGGGATGCAGCCATCATGAAGATGACCAAGGAGGCTGGTGTGGAAGT
         F  G  K  E  R  D  A  A  I  M  K  M  T  K  E  A  G  V  E  V
        430             450             470

AGTGACGGAGAATTCTCATACCCTCTATGACCTGGACAGGATGATTGAGCTGAATGGGCA
         V  T  E  N  S  H  T  L  Y  D  L  D  R  I  I  E  L  N  G  Q
        490             510             530

GAAGCCACCCCTTACATACAAGCGCTTTCAGGCCATCATCAGCCGCATGGAGCTGCCCAA
         K  P  P  L  T  Y  K  R  F  Q  A  I  I  S  R  M  E  L  P  K
        550             570             590

GAAGCCAGTGGGCTTGGTGACCAGCCGGCAGATGGAGAGCTGCAGGGCCGAGATCCAGGA
         K  P  V  G  L  V  T  S  R  Q  M  E  S  C  R  A  E  I  Q  E
        610             630             650

GAACCACGACGAGACCTACGGCGTGCCCTCCCTGGAGGAGCTGGGGTTCCCCACTGAAGG
         N  H  D  E  T  Y  G  V  P  S  L  E  E  L  G  F  P  T  E  G
        670             690             710

ACTTGGTCCAGCTGTCTGGCAGGGAGGAGAGACAGAAGCTCTGGCCCGCCTGGATAAGCA
         L  G  P  A  V  W  Q  G  G  E  T  E  A  L  A  R  L  D  K  H
        730             750             770
```

FIG. 1A

```
CTTGGAACGGAAGGCCTGGGTTGCCAACTATGAGAGACCCCGAATGAACGCCAACTCCCT
 L  E  R  K  A  W  V  A  N  Y  E  R  P  R  M  N  A  N  S  L
790                   810                   830

CCTGGCCAGCCCCACAGGCCTCAGCCCCTACCTGCGCTTTGGTTGTCTCTCCTGCCGCCT
 L  A  S  P  T  G  L  S  P  Y  L  R  F  G  C  L  S  C  R  L
850                   870                   890

CTTCTACTACCGCCTGTGGGACCTGTATAAAAAGGTGAAGCGGAACAGCACACCTCCCCT
 F  Y  Y  R  L  W  D  L  Y  K  K  V  K  R  N  S  T  P  P  L
910                   930                   950

CTCCCTATTTGGGCAACTCCTATGGCGAGAGTTCTTCTACACGGCAGCTACCAACAACCC
 S  L  F  G  Q  L  L  W  R  E  F  F  Y  T  A  A  T  N  N  P
970                   990                   1010

CAGGTTTGACCGCATGGAGGGGAACCCCATCTGCATCCAGATCCCCTGGGACCGCAATCC
 R  F  D  R  M  E  G  N  P  I  C  I  Q  I  P  W  D  R  N  P
1030                  1050                  1070

TGAGGCCCTGGCCAAGTGGGCTGAGGGCAAGACAGGCTTCCCCTTGGATTGATGCCATCAT
 E  A  L  A  K  W  A  E  G  K  T  G  F  P  W  I  D  A  I  M
1090                  1110                  1130

GACCCAACTGAGGCAGGAGGGCTGGATCCACCACCTGGCCCGGCATGCCGTGGCCTGCTT
 T  Q  L  R  Q  E  G  W  I  H  H  L  A  R  H  A  V  A  C  F
1150                  1170                  1190

CCTGACCCGCGGGGACCTCTGGGTCAGCTGGGAGAGCGGGGTCCGGGTATTTGATGAGCT
 L  T  R  G  D  L  W  V  S  W  E  S  G  V  R  V  F  D  E  L
1210                  1230                  1250

GCTCCTGGATGCAGATTTCAGCGTGAACGCAGGCAGCTGGATGTGGCTGTCCTGCAGTGC
 L  L  D  A  D  F  S  V  N  A  G  S  W  M  W  L  S  C  S  A
1270                  1290                  1310

TTTCTTCCAGCAGTTCTTCCACTGCTACTGCCCTGTGGGCTTTGGCCGTCGCACGGACCC
 F  F  Q  Q  F  F  H  C  Y  C  P  V  G  F  G  R  R  T  D  P
1330                  1350                  1370

CAGTGGGGACTACATCAGGCGATACCTGCCCAAATTGAAAGCGTTCCCCTCTCGATACAT
 S  G  D  Y  I  R  R  Y  L  P  K  L  K  A  F  P  S  R  Y  I
1390                  1410                  1430

CTATGAGCCCTGGAATGCCCCAGAGTCAATTCAGAAGGCAGCCAAGTGCATCATTGGTGT
 Y  E  P  W  N  A  P  E  S  I  Q  K  A  A  K  C  I  I  G  V
1450                  1470                  1490

GGACTACCCACGGCCCATCGTCAACCATGCCGAGACCAGCCGGCTTAACATTGAACGAAT
 D  Y  P  R  P  I  V  N  H  A  E  T  S  R  L  N  I  E  R  M
1510                  1530                  1550

GAAGCAGATTTACCAGCAGCTTTCGCGCTACCGGGGACTCTGTCTACTGGCATCTGTCCC
 K  Q  I  Y  Q  Q  L  S  R  Y  R  G  L  C  L  L  A  S  V  P
1570                  1590                  1610

TTCCTGTGTGGAAGACCTCAGTCACCCTGTGGCAGAGCCCAGCTCGAGCCAGGCTGGCAG
 S  C  V  E  D  L  S  H  P  V  A  E  P  S  S  S  Q  A  G  S
```

FIG.1B

```
                1630                1650                1670
        CATGAGCAGTGCAGGCCCAAGACCACTACCCAGTGGCCCAGCATCCCCCAAACGCAAGCT
          M  S  S  A  G  P  R  P  L  P  S  G  P  A  S  P  K  R  K  L
                1690                1710                1730
        GGAAGCAGCCGAGGAACCACCTGGTGAAGAACTCAGCAAACGGGCCCGGGTGGCAGAGTT
          E  A  A  E  P  P  G  E  E  L  S  K  R  A  R  V  A  E  L
                1750                1770                1790
        GCCAACCCCAGAGCTGCCGAGCAAGGATGCCTGAGACTGCAGAGCCCTTGCTCCGTGAGC
          P  T  P  E  L  P  S  K  D  A  *
                1810                1830                1850
        AAAGCCTGGGTGCCCAAGCAGCCACCGCAGCAGCAGAGTACAACCTGCAGAGAAGCTGAT
                1870                1890                1910
        CACCGGGCAGAGATAGAGCGAGCATGTGTGTGTGTGCGCGTGTGCAGAGGAGGGAGTG
                1930                1950                1970
        GTGTGCCTGTTTGTGTGTGCATGCATCTGTTGACACTCATGATTCTGAATGTTGCCTGGG
                1990                2010                2030
        CTGGGGGAGTACCTGTAGCACGCCAGTGCTGTTTCCCGGCCTCCGAGCACAAGGCTCGAG
                2050                2070                2090
        GTTATGGCAGTGACTTTCAGCTGAGACCTGTTCCTGCAAGCCAGCTGCCTTGTCTGAACA
                2110                2130                2150
        GAACGTAGTGGTAGGACCCTAGCTGGGATTCTGGCATCTGCCTCCCTAGACCTCCTTCCC
                2170                2190                2210
        TCCCTCCTCACGTCAGGCTGTGGAGCAGGAGCACAGCAGTTCTGGCTGTTGTCCAAAGCA
                2230                2250                2270
        TGGGATTCTGGAGGCAGCCAGAGCCCTGCTGAGTTCCTGCTTTCTGACCTGGAGGCTGAG
                2290                2310                2330
        CAGGCCGGAGTGGATGGATGCTGTCCAGACGTAGCCACCTGGCCTCTGTTTCTTATTTTA
                2350                2370                2390
        AAATTCTCTGCTACTGGGCTGAGTCCCAGGCCCTTCCTTGGGCTTCTGGGACTGAGCATG
                2410                2430                2450
        AGGCCATAGACAGATCTAAAAAGTTTCCACCACCCTACAGAAGTACACACAGATACCTGA
                2470                2490                2510
        CTGGTGTGGGGTATGCCTGGTACTGTAATAGGAGCCTAAGACAGCACACCTACCTTTTCA
                2530                2550                2570
        GGATTTAGAACCTAAAATTAGAAAGAGAATCCCAGCTGTCATTGTTCCTTCCCCAGAAGC
                2590                2610                2630
        TAAGAGCCAGCCTCAGAGCCTACCCAGGAGCTGTGAAGGGGCAAGGGTCAAACTGACTCA
                2650                2670                2690
        CTCTACCAGGAGGAGACCAGGTTGCAGTGGCGTAAGGCCCCCTGGTTTCTCTGGCCACAC
                2710                2730                2750
```

FIG. 1C

```
TCCAAGGCACCACAGTGCTGCCAGTGAGGACAGCTGACACCCAGCCAGGGAAACCATTCT
2770                    2790                    2810
AGTCTTTATTCTGTTGGCTTCCAGGGCCTGTCCTGAACTTGTCAGCATCCAGACTGCCAT
2830                    2850                    2870
GTCAGCTATCCCAGTAGCTGAGCTCCAAGGACTCAGGCAGAGGGACTCAGGGATGGGGAC
2890                    2910                    2930
TGCCAGGGGCAGTTGGCAAAAGTCCAAGTAGAGATTACACCCAGAACACCATTCCTTCCA
2950                    2970                    2990
GGAGCAGTAGGTGGGAGGTTTGACCCAGAGAAGCCAATCCTTGCATTCCAGGAGTGGCCT
3010                    3030                    3050
GTGCCTCCCACCTCTTCCTTCCCACTGCCAAAGGCCTGTGTTGAGAAAGATGTCATGCAA
3070                    3090                    3110
AAGGACGACGGTGGCCAACTAAAGCAAGTCTTCCTACCACCCTGTGGCCTGCACTTGAGC
3130                    3150                    3170
CACAAAGTGTGTGTGTGTGTGCGTGTGTGGTAAGTGTGTGTGTGTGTGGCTATGAGGC
3190                    3210                    3230
TGATTCCTGTTTGGATTTTTTGTCCTCACGTGTATCATTAAGCTGGCCTTTGGGCCTTTTC
3250                    3270                    3290
CTTTCTACCTCCCCTGTGACCTTTCCTAGCCTCAGATCTGTTAATTCTTTTGGCCCCAGC
3310                    3330                    3350
CCTGTCCCTCACTGTCCTCTGTCCTTGGACCAGAACCCTGGGGTCAGACCCATGTCCTGT
3370                    3390                    3410
AGCTGTCCATCACACTGACAGGCTTCTTCCTGAGATATCCTCAGGTTTTCTCAGCCAGAG
3430                    3450                    3470
AGCTGCCTTTAGAGTCCAACTGTTGTACGTATGTCACCTTCACTAGAAATGTCCCATCAT
3490                    3510                    3530
CGTGGGAGGGGAGCAGGGCACAGGGGATGGTGTGCATTCAGAGCATTGGGTTGGGGGCTT
3550                    3570                    3590
CCCTGTTCCCTCAGCCCCAGTCGAGAGGAAAGAGAATCGGGCCACTGCCAGAAAGAGAGT
3610                    3630                    3650
CAAAGCAAACCTGGAAGGGCAAATCTGAGAGTGGGAAGGCCAAAGGCCGAGGCCCAGAAA
3670                    3690                    3710
AGTATTCACTAGCAGCGCCTTCGGGTAGCAGGATGATTCCTTTTCCTGCCTGTCTGCTGC
3730                    3750                    3770
TGGCTCTCTTCCCTAAGGTACAGGTTGGCAGGACCACCTCCGCCTACTTCTCCACCATCC
3790                    3810                    3830
CTAGCATGCCAGCCCGTTCCCAGATCAACCTGCCAGTGGAGTCAGGCAGTGCACTCCTGG
3850                    3870                    3890
```

FIG.1D

```
AGCCAAGAGGGAAGGGCAGGGTAGAGAGGGTATGTCCAGTAGCCTGGAGCTCCATGGTGG
3910                    3930                3950

CTTCATGCCTCCCTTCTCCCAGCTCAGGTGGCCCTGAGGGCTCCCTCGGAACAGTGCCTC
3970                    3990                4010

AAATCCTGACCCAAGGGCCAGCATGGGGAAGAGATGGTTGCAGGCAAAATGCACTTTATA
4030                    4050                4070

GAGATTTTCTATTGCTGGGAAGGTGTGTTTCTCCCACAATTTGTTTGTGAATATTCACTT
4090                    4110                4130

GTTTTATAAATGTCTGACCTGTCTTGAGTAAAAAAAAAAAAAAAAAAAAA
```

FIG. 1E

```
hCRY1   2 GVNAVHWFRKGLRLHDNPALKECIQGADTIRCVYILDPWFAGSSNVGINR  51
            :...|||||||||||||||  ..:.||  .:||||||||||||:||.|||||
hCRY2  21 SASSVHWFRKGLRLHDNPALLAAVRGARCVRCVYILDPWFAASSSVGINR  70

52 WRFLLQCLEDLDANLRKLNSRLFVIRGQPADVFPRLFKEWNITKLSIEYD 101
          ||||||:|||||..||||||||||:|||||||||||||||.:|:|.:|.|
       71 WRFLLQSLEDLDTSLRKLNSRLFVVRGQPADVFPRLFKEWGVTRLTFEHD 120

102 SEPFGKERDAAIKKLATEAGVEVIVRISHTLYDLDKIIELNGGQPPLTYK 151
          ||||||||||||.|:...||||||:.  ||||||||:||||||..|||||
      121 SEPFGKERDAAIMKMTKEAGVEVVTENSHTLYDLDRIIELNGQKPPLTYK 170

152 RFQTLISKMEPLEIPVETITSEVIEKCTTPLSDDHDEKYGVPSLEELGFD 201
          |||.:||:||  .||:  :||   :|.|  ...: ::|||.||||||||.
      171 RFQAIISRMELPKKPVGLVTSRQMESCRAEIQENHDETYGVPSLEELGFP 220

202 TDGLSSAVWPGGETEALTRLERHLERKAWVANFERPRMNANSLLASPTGL 251
          |:||:.|||.||||||||.||::|||||||||:|||||||||||||||||
      221 TEGLGPAVWQGGETEALARLDKHLERKAWVANYERPRMNANSLLASPTGL 270

252 SPYLRFGCLSCRLFYFKLTDLYKKVKKNSSPPLSLYGQLLWREFFYTAAT 301
          ||||||||||||||::|  |||||||:||.|||||:||||||||||||||
      271 SPYLRFGCLSCRLFYYRLWDLYKKVKRNSTPPLSLFGQLLWREFFYTAAT 320

302 NNPRFDKMEGNPICVQIPWDKNPEALAKWAEGRTGFPWIDAIMTQLRQEG 351
          ||||||:||||||||:|||||:|||||||||||:||||||||||||||||
      321 NNPRFDRMEGNPICIQIPWDRNPEALAKWAEGKTGFPWIDAIMTQLRQEG 370

352 WIHHLARHAVACFLTRGDLWISWEEGMKVFEELLLDADWSINAGSWMWLS 401
          ||||||||||||||||||||:.|::|:|||||||:|:|||||||||||||
      371 WIHHLARHAVACFLTRGDLWVSWESGVRVFDELLLDADFSVNAGSWMWLS 420

402 CSSFFQQFFHCYCPVGFGRRTDPNGDYIRRYLPVLRGFPAKYIYDPWNAP 451
          ||.||||||||||||||||||||.|||||||| |::||.:|||:|||||
      421 CSAFFQQFFHCYCPVGFGRRTDPSGDYIRRYLPKLKAFPSRYIYEPWNAP 470

452 EGIQKVAKCLIGVNYPKPMVNHAEASRLNIERMKQIYQQLSRYRGLGLLA 501
          |:|||.|||:|||:||:|:|||||.||||||||||||||||||||||.|||
      471 ESIQKAAKCIIGVDYPRPIVNHAETSRLNIERMKQIYQQLSRYRGLCLLA 520

502 SVPSNPNGNGGFMGYSAENIPGCSSSGSCSQGSGILHYAHGDSQQTHLLK 551
          ||||        :.|:::. ...|:||::::      .|...:. |.
      521 SVPS........CVEDLSHPVAEPSSSQAGSM......SSAGPRPLP 553

552 QGRSSMGTGLSGGKRPSQEEDTQSIGPKVQRQST 585
          |..|   |:.:.  |..||  |   :|.   .|
      554 SGPASPKRKLEAAEEPPGEE...LSKRARVAELPT 585
```

FIG. 2

```
E.c.                                                                                         M     1
A.t.                                                                                 M SGSVSGCGSG  11
D.m.                                                                                        MDSQR   5
hCRY1                                                                                          MG   2
hCRY2                                                               M AATVATAAAV APAPAPGTDS        21

E.c.   TTHLVWFRQD LRLHDNLALA AACRNSSAR.  .....VLALYI ATPRQWATHN MSPRQAELIN AQLNGLQIAL            66
A.t.   GCSLVWFRRD LRVEDNPALA AAVR..AGP.  .....VIALFV WAPEEEGHYH PGRVSRWWLK NSLAQLDSSL            74
D.m.   STLVHWFRKG LRLHDNPALS HIFTAANAAP GKYFVRPIFI LDPGILDWMQ VGANRWRFLQ QTLEDLDNQL             75
hCRY1  VNAVHWFRKG LRLHDNPALK ECIQGADT..  ......IRCVYI LDPWFAGSSN VGINRWRFLL QCLEDLDANL            66
hCRY2  ASSVHWFRKG LRLHDNPALL AAVRGARC..  ......VRCVYI LDPWFAASSS VGINRWRFLL QSLEDLDTSL            85

E.c.   AEKGIPLLFR EVDDFVAS.V EIVKQVCAEN SVTHLFYNYQ YEV.......NE RARDVEVERA LRNVVCEG..           128
A.t.   RSLGTCLITK RSTDSVASLL DVVKSTGA..  ..SQIFFNHL YDPLSLVRDH RAKDVLTAQC ...LAVRS...          135
D.m.   RKLNSRFVV  RGKP......A EVFPRIFKSW RVEMLTFETD IEPYSVTRDA AVQKLAKAEG VRVETHCSHT           140
hCRY1  RKLNSRLFVI RGQP......A DVFPRLFKEW NITKLSIEYD SEPFGKERDA AIKKLATEAG VEVIVRISHT           131
hCRY2  RKLNSRLFVV RGQP......A DVFPRLFKEW GVIRLTFEYD SEPFGKERDA AIMKMAKEAG VEVVTENSHT           150

E.c.   .FDDSVILPP GAVMTGNHEM YKVFTPFKNA WLKRLREGMP ECVAAPKVRS SGSIEPSPSI TLNYP..RQS            195
A.t.   .FNADLLYEP WEVTDELGRP FSMFAAFWE. RCLSMPYDPE SPLLPPKKII SGDVSKCVAD PLVFE..DDS            201
D.m.   IYNPELVKAK NLGKAPI..T YQKFLGIVEQ LKVPKVLGVP EKLKKMPTPP KDEVEQKDSA AYDCPTIKQL            208
hCRY1  LYDLDKIIEL NGGQPPL..T YKRFQTLISK MEPLEI.PVE TITSEVIEKC TPPLSDDHDE KYGVPSLEEL            198
hCRY2  LYDLDRIIEL NGQKPPL..T YKRFQAIISR MELPKK.PVG LVTSQQMESC RAEIQENHDE TYGVPSLEEL            217
```

FIG.4A

| | | | | | | | |
|---|---|---|---|---|---|---|---|
| E.c. | FDTAH...... | .FPVEEKAAI | AQLRQFCQNG | A..GEYEQQR | DFPAV..EGT | SRLSASLATG | GLSPPQCLHR 255 |
| A.t. | EKGSNALLAR | AWSPGWSNGD | KALTTFINGP | L..LEYSKNR | RKADS..ATT | SELSPHLHFG | EVSVPKVFHL 267 |
| D.m. | VKRPEELGPN | KFPGGETEAL | RRMEESLKDE | IWVARFEKPN | TAPNSLEPST | TVLSPYLKFG | CLSAPLFNQK 278 |
| hCRY1 | GFDTDGLSSA | VWPGGETEAL | TRLERHLERK | AWVANFERPR | MNANSLLASP | TGLSPYLRFG | CLSCPLFYFK 268 |
| hCRY2 | GFPTEGLGPA | VWQGGETEAL | ARLDKHLERK | AWVANYERPR | MNANSLLASP | TGLSPYLRFG | CLSCPLFYYR 287 |
| | | | | | | | |
| E.c. | L........LAE | QPQALDGGAG | SVWLNELIWR | EFYRHLITYH | PSLCKHRPFI | AWTDRVQWQS | NPAHLQAWQE 319 |
| A.t. | VRIKQVAWAN | EGNEAGEESV | NLFLKSIGIR | EYSR.YISFN | HPYSHERPLL | GHLKFFPWAV | DENYFKAWRQ 226 |
| D.m. | LKEIIKRQPK | HSQPPVS... | ..LIGQLMWR | EFYTVAAAE | PNFDRMLGNV | YCMQ.IPWQE | HPDHLEAWTH 342 |
| hCRY1 | LTDLYKKVKK | NSSPPLS... | ..LYGQLLWR | EFFYTAATNN | PRFDKMEGNP | ICVQ.IPWDK | NPEALAKWAE 332 |
| hCRY2 | LWDLYKKVKR | NSTPPLS... | ..LFGQLLWR | EFFYTAATNN | PRFDRMEGNP | ICIQ.IPWDR | NPEALAKWAE 351 |
| | | | | | | | |
| E.c. | GKTGYPIVDA | AMRQLNSTGW | MHNRLRMITA | SFLVK.DLLI | DWREGERYFM | SQLLDGDLAA | NNGGMQWAAS 388 |
| A.t. | GRTGYPLVDA | GMRELWATGW | IHDRIRVVVS | SFFVK.VLQL | DWRWGMKYFW | DTLLDADLES | DALGWQYITG 405 |
| D.m. | GRTGYPF IDA | IMRQLRQEGW | IHHLARHAVA | CFLTRGDLWI | SWEEGQRVFE | QLLLDQDWAL | NAGNMWWLSA 412 |
| hCRY1 | GRTGFPWIDA | IMTQLRQEGW | IHHLARHAVA | CFLTRGDLWI | SWEEGMKVFE | ELLLDADWSI | NAGSWMWLSC 402 |
| hCRY2 | GRTGFPWIDA | IMTQLRQEGW | IHHLARHAVA | CFLTRGDLMV | SWESGVRVFD | ELLLDADFSV | NAGSWMWLSC 421 |
| | | | | | | | |
| E.c. | TGTDAAPYFR | IFNPTTQGEK | FDHEGEFIRQ | WLPELRDVPG | KVVHEPWKWA | ....QKAGVT | L..DYPQPIM 452 |
| A.t. | TLPDSREFDR | IDNPQFEGYK | FDPNGEYVRR | WLPELSRLPT | DWIHHPWNAP | ESVLQAAGIE | LGSNYPLPIV 475 |
| D.m. | SAF.FHQYFR | VYSPVAFGKK | TDPQGHYIRK | YVPELSKYPA | TCIYEPWKAS | LVDQRAYGCV | LGTDYPHRIV 481 |
| hCRY1 | SSF.FQQFFH | CYCPVGFGRR | TDPNGDYIRR | YLPVLRGFPA | KYIYDPWNAP | EGIQKVAKCL | IGVNYPKPMV 471 |
| hCRY2 | SAF.FQQFFH | CYCPVGFGRR | TDPSGDYIRR | YLPKLKAFPS | RYIYEPWNAP | ESIQKAAKCI | IGVDYPRPIV 490 |

FIG.4B

```
E.c.    EHKEARVQTL AA.......YE AARKGK*                                                                              473
A.t.    GLDEAKARLH EALSQMWQLE AASRAAIENG SEEGLGDSAE VEEAPIEFPR DITMEETEPT RLNPNRRYED                                 545
D.m.    KHEVVHKENI KRMGAAYK.. .......... VNREVRT GKEEESSFEE KSETSTSGKR KVRRATGSAP                                    536
hCRY1   NHAEASRLNI ERMKQIYQQL SRYRGLGLLA SVPSNPNGNG GFMGYSAENI PGCSSSGS.. ...CSQGSGI                                 536
hCRY2   NHAETSRLNI ERMKQIYQQL SRYRGLCLLA SVPSCVEDLS HPVAEPSSSQ AGSMSSAGPR PLPSGPASPK                                 560

A.t.    QMVPSITSSL IRPEEDEESS LNLRNSVGDS RAEVPRNMVN TNQAQQRRAE PASNQVTAMI PEFNIRIVAE                                  615
D.m.    KRKR*                                                                                                       540
hCRY1   LHYAHGDSQQ THLLKQGRSS MGTGLSGGKR PSQEE.DTQS IGPKVQRQST N*                                                    586
hCRY2   RKLEAAEEPP GEEL...SKRA RVAELPTPEL PSKDA*                                                                     593

A.t.    STEDSTAESS SSGRRERSGG IVPEWSPGYS EQFPSEENRI GGGSTTSSYL QNHHEILMWR RLSQTG*                                     681
```

FIG.4C

HUMAN BLUE-LIGHT PHOTORECEPTOR HCRY2

CROSS-REFERENCE TO RELATED APPLICATIONS

This application is a divisional of U.S. appl. Ser. No. 08/964,268, filed Nov. 4, 1997, now U.S. Pat. No. 6,114,503, which claims the benefit of U.S. appl. Ser. No. 60/030,189, filed Nov. 4, 1996, which disclosure is herein incorporated by reference.

BACKGROUND OF THE INVENTION

1. Field of the Invention

The present invention relates to a novel human blue-light photoreceptor. More specifically, isolated nucleic acid molecules are provided encoding a human blue-light photoreceptor. Human blue-light photoreceptor polypeptides are also provided, as are vectors, host cells, antibodies, and recombinant methods for producing the same.

2. Related Art

In many organisms, the photolyase/photoreceptor family of proteins mediates DNA repair. In plants, certain developmental processes are regulated by blue-light. This regulation occurs by a photoinduced electron transfer reaction (Taylor, J. S., *Acc. Chem. Res.* 27:76–82 (1994); Menkens, A. E. et al., *Biochemistry* 34:6892–6899 (1995); Heelis, P. F. et al., *Photochem. Photobiol.* 95:89–98 (1996); and Sancar A., *Science* 272:48–49 (1996)). Indeed, to date, most of the work concerning blue-light photoreceptors has been conducted in plants (Cashmore, A. R. et al., *International Patent Application* WO 96/01897 (1996); Hinnemann, H., *Photochem. Photobol.* 61:22–31(1995); Short, T. W. et al., *Annu. Rev. Plant. Physiol. Plant Mol. Biol.* 45:143–171 (1994); Hohl, N. et al., *Photochem. Photobiol.* 55:239–245 (1992)) and fungi (Dunlap, J. C., *Annu. Rev. Physiol.* 55:683–728 (1993)). In plants, blue-light induces responses such as photomorphogenesis, phototropism and hypocotyl elongation. In particular, it has been demonstrated that the HY4 gene of *A. thaliana*, which encodes the CRY1 protein, is required for blue-light induced hypocotyl elongation (Ahmad, M., et al., *Nature* 366:162–166 (1993)).

In animals, most of the work on light response (other than vision) has been concentrated on circadian clocks. In *D. melanogaster*, two genes have been cloned, timeless and period, which regulate the circadian rhythm (Myers, M. P. et al., *Science* 270:805–808 (1995); Gekakis, N. et al., *Science* 270:811–814 (1995)). Both appear to be transcription factors for which activity is regulated by light. A mutation in the golden hamster tau gene disrupts the circadian clock Ralph and Menaker, 1988). Three mouse genes, CLOCK, ICER, and CREM, which are involved in the control of circadian rhythm, have been investigated in some detail (Vitaterna et al., M. H. et al., *Science* 264:719–725 (1994); Sassone-Corsi P. A, *Rev. Cell Dev. Biol.* 11:355–377 (1995); Foulkes, N. S. et al., *Nature* 381:83–85 (1996)). Each of these three gene products appears to be a transcriptional repressor for which activity is regulated by light. However, how the light signal is transmitted to these transcriptional regulators is not known.

Currently, the photolyase/photoreceptor protein family is known to contain three members: the cyclobutane pyrimidine dimer (Pyr< >Pyr) photolyase (photolyase), the (6-4) photolyase, and the blue-light photoreceptor (Todo, T. et al., *Science* 272:109–112 (1996)). The gene for the classical Pyr< >Pyr photolyase has been cloned and the enzyme has been purified from many organisms, including *Escherichia coli, Saccharomyces cerevisiae, Drosophila melanogaster,* and *Carassius auratus* (Sancar, A, *Mutation Res.* 236:147–160(1990); Kato, T. et al., *Nucl. Acids Res.* 22:41194124 (1994); and Yasui, A et al., *EMBO J.* 13:6143–6151 (1994). The (6-4) photolyase has been found in *D. melanogaster* (Todo, T. et al., *Nature* 361:371–374 (1993); Kim, S. T. et al., *J. Biol. Chem.* 269:8535–8540 (1994)), *Xenopus laevis,* and *Crotalus atrox* (Kim, S. T. et al., *Photochem. Photobiol.* 63:292–295 (1996)).

Concerning the cloning of (6-4) photolyase genes, only the Drosophila gene has been cloned and sequenced (Todo, T. et al., *Science* 272:109–112 (1996)). The genes for the apoproteins of the blue-light photoreceptors of *Arabidopsis thaliana* (Ahmad, M., *Nature* 366:162–166 (1993)), *Sinapis alba* (Batschauer, A, *Plant J.* 4:705–709 (1993); Malhotra, K. et al., *Biochemistry* 34:6892–6899 (1995)), and *Chlamydomonas reinhardtii* (Small, G. D., et al., *Plant Molec. Biol.* 28:433–454 (1995)) have been cloned and sequenced. The photoreceptors of *A. thaliana* (Malhotra, K. et al., *Biochemistry* 34:6892–6899 (1995); Lin, C. et al., *Science* 269: 968–970 (1995)) and *S. alba* (Malhotra, K. et al., *Biochemistry* 34:6892–6899 (1995)) have been purified and characterized.

Circadian regulation of human and animal physiology, and particularly circadian regulation mediated by blue-light photoreceptors, is poorly understood. Thus, there is a need for an isolated human blue-light photoreceptor gene, the polypeptide encoded by that gene, and antibodies specific for that polypeptide.

SUMMARY OF THE INVENTION

The present invention provides isolated nucleic acid molecules comprising a polynucleotide encoding the human blue-light photoreceptor hCRY2 [hereinafter "hCRY2"] receptor having the amino acid sequence shown in SEQ ID NO:2 or the amino acid sequence encoded by the cDNA clone deposited in a bacterial host as ATCC Deposit Number 97769 on Oct. 22, 1996.

The present invention also relates to recombinant vectors, which include the isolated nucleic acid molecules of the present invention, to host cells containing the recombinant vectors, to host cells containing an isolated polypeptide, as well as to methods of making such vectors and host cells and for using them for production of hCRY2 polypeptides or peptides by recombinant techniques.

The invention further provides an isolated hCRY2 polypeptide having an amino acid sequence encoded by a polynucleotide described herein.

The invention further provides isolated antibodies that bind specifically to the full length hCRY2 receptor, the mature hCRY2 receptor, the hCRY2 receptor extracellular domain, the hCRY2 receptor transmembrane domain, the hCRY2 receptor intracellular domain, and epitope-bearing portions of the hCRY2 receptor.

BRIEF DESCRIPTION OF THE FIGURES

FIGS. 1A–1E show the nucleotide (SEQ ID NO:1) and deduced amino acid (SEQ ID NO:2) sequences of hCRY2 receptor. The protein has a predicted leader sequence of about 22 amino acid residues (underlined) and a deduced molecular weight of about 81 kDa. It is further predicted that amino acid residues from about 23 to about 514 (about 1 to about 492 in SEQ ID NO:2) constitute the extracellular domain; from about 515 to about 527 (about 493 to about 505 in SEQ ID NO:2) the transmembrane domain; and from about 528 to about 593 (about 506 to about 571 in SEQ ID NO:2) the intracellular domain.

FIG. 2 shows the regions of similarity between the amino acid sequences of the hCRY2 receptor protein and hCRY1 (SEQ ID NO:3).

FIGS. 4A–C show the sequence comparison of *E. coli* photolyase (*E.c.*) (SEQ ID NO:4), Arabidopsis HY4 photoreceptor (*A.t.*) (SEQ ID NO:5), *Drosophila melanogaster* (6-4) photolyase (*D.m.*) (SEQ ID NO:6), and the human blue-light photoreceptors hCRY1 (SEQ ID NO:3) and hCRY2 (SEQ ID NO:2). Amino acid residues which are identical in the entire set are boxed.

DETAILED DESCRIPTION

Figure 3:
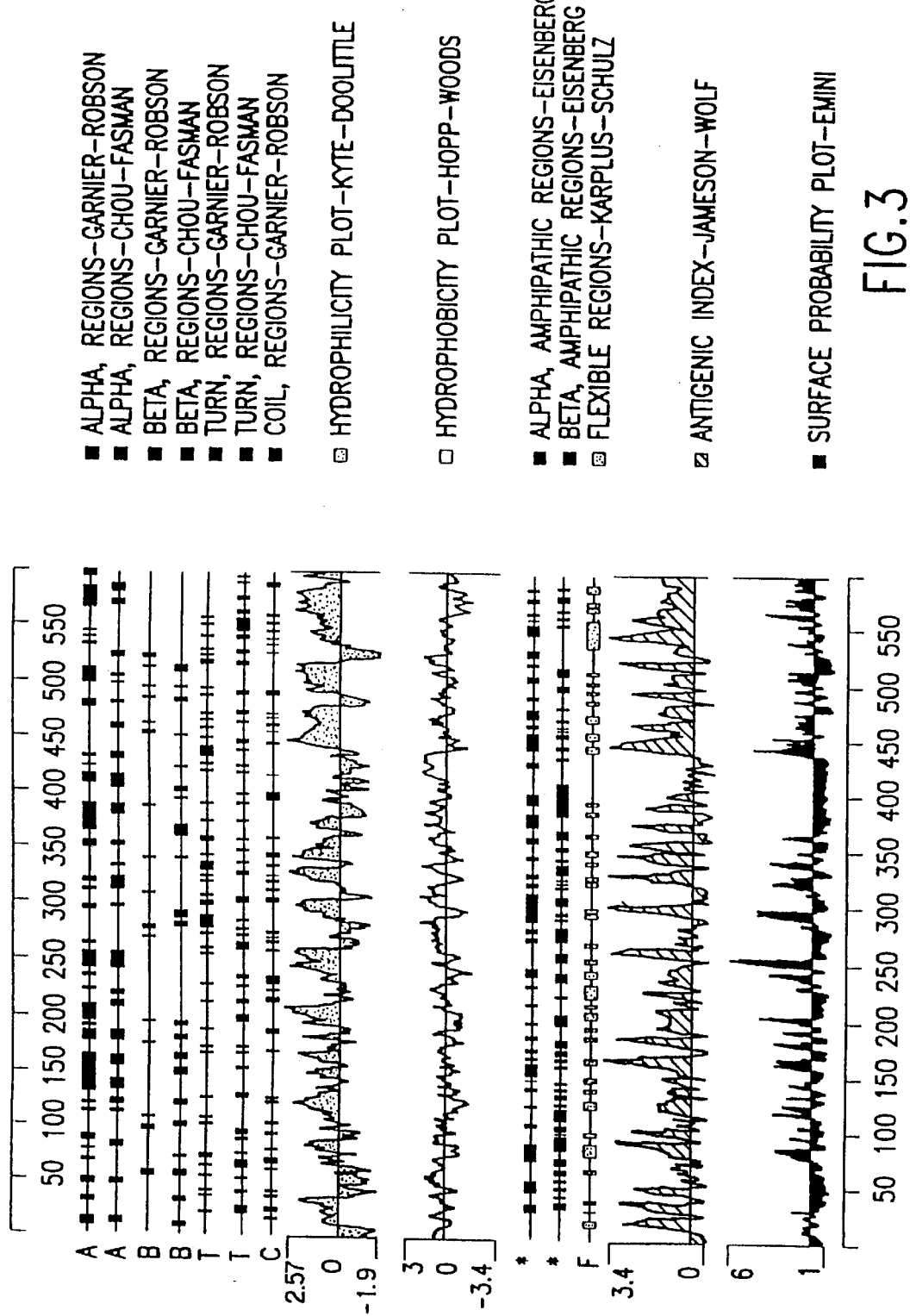
FIG. 3 shows an analysis of the hCRY2 receptor amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 30 to about 39, about 45 to about 52, about 77 to about 92, about 96 to about 103, about 158 to about 169, about 178 to about 187, about 253 to about 261, about 293 to about 301, about 320 to about 331, about 338 to about 346, about 350 to about 356, about 437 to about 448, and about 534 to about 541 in FIG. 1 correspond to the shown highly antigenic regions of the hCRY2 receptor protein. These highly antigenic fragments in FIG. 1 correspond to the following fragments, respectively, in SEQ ID NO:2: amino acid about 8 to about 17, about 23 to about 30, about 55 to about 70, about 74 to about 81, about 136 to about 147, about 156 to about 165, about 231 to about 239, about 271 to about 279, about 298 to about 309, about 316 to about 324, about 328 to about 334, about 415 to about 426, and about 512 to about 519.

The present invention provides isolated nucleic acid molecules comprising a polynucleotide encoding a hCRY2 polypeptide having the amino acid sequence shown in SEQ ID NO:2. The amino acid sequence was deduced from the sequence of a cloned hCRY2 cDNA. The sequenced cDNA clone was obtained using RACE-PCR (infra). The hCRY2 protein of the present invention shares sequence homology with hCRY1 (FIG. 2; SEQ ID NO:3).

A cDNA encoding a maltose binding protein-hCRY2 fusion protein, including amino acid residues –15 to 571 (SEQ ID NO:2) was deposited on Oct. 22, 1996 at the American Type Culture Collection Patent Depository, 10801 University Boulevard, Manassas, Va. 20110-2209; and given accession number 97769. The hCRY2 sequence is contained between the EcoR V and Hind III sites in the polylinker of the Mal-C2 vector (NEB, Beverly, Mass.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO:1, a nucleic acid molecule of the present invention encoding a hCRY2 polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from human fetal brain. The hCRY2 gene was also identified in cDNA libraries from the following tissues: synovial sarcoma, resting T-cell, infant brain, cerebellum, endometrial tumor, testes tumor, adult retina, chondrosarcoma, breast, and pituitary.

The determined nucleotide sequence of the hCRY2 cDNA of SEQ ID NO:1 contains an open reading frame encoding a protein of about 593 amino acid residues, with a predicted leader sequence of about 22 amino acid residues, and a deduced molecular weight of about 81 kDa The hCRY2 protein shown in SEQ ID NO:2 is about 74% identical and about 85% similar to hCRY1 (FIG. 2; SEQ ID NO:3).

As indicated, the present invention also provides the mature form(s) of the hCRY2 receptor of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature hCRY2 polypeptides having the amino acid sequence encoded by the cDNA clone contained in the host identified as ATCC Deposit No. 97769 and as shown in SEQ ID NO:2. By the mature hCRY2 protein having the amino acid sequence encoded by the cDNA clone contained in the host identified as ATCC Deposit 97769 is meant the mature form(s) of the hCRY2 receptor produced by expression in a mammalian cell (e.g., COS cells, as described below) of the open reading frame encoded by the human DNA sequence of the clone contained in the vector in the deposited host. This clone lacks amino acid residues −22 to−16 in SEQ ID NO:2. As indicated below, the mature hCRY2 receptor having the amino acid sequence encoded by the cDNA clone contained in ATCC Deposit No. 97769 may or may not differ from the predicted "mature" hCRY2 protein shown in SEQ ID NO:2 (amino acids from about 1 to about 571) depending on the accuracy of the predicted cleavage site.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete hCRY2 polypeptide of the present invention was analyzed by a computer program ("PSORT") (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 27 and 28 in SEQ ID NO:2. However, based on homology to the hCRY1 protein (FIG. 2; SEQ ID NO:3), the cleavage site is predicted to be between amino acids −1 and 1 in SEQ ID NO:2. Thus, the leader sequence for the hCRY2 protein is predicted to consist of amino acid residues −1 to −22 in SEQ ID NO:2, while the mature hCRY2 protein is predicted to consist of amino acids residues 1–571 in SEQ ID NO:2.

As one of ordinary skill would appreciate, however, due to the possibilities of sequencing errors, as well as the variability of cleavage sites for leaders in different known proteins, the full-length hCRY2 polypeptide comprises about 593 amino acids, but may be anywhere in the range of about 580 to about 600 amino acids; and the leader sequence is about 22 amino acids, but may be anywhere in the range of about 15 to about 55 amino acids.

As indicated, nucleic acid molecules of the present invention may be in the form of RNA, such as mRNA, or in the form of DNA, including, for instance, cDNA and genoric DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or m vitro RNA transcripts of the DNA molecules of the present invention. Isolated nucleic acid molecules according to the present invention further include such molecules produced synthetically.

Isolated nucleic acid molecules of the present invention include DNA molecules comprising the open reading frame (ORF) shown in SEQ ID NO:1; DNA molecules comprising the coding sequence for the mature hCRY2 receptor shown in SEQ ID NO:2; and DNA molecules which comprise a sequence substantially different from those described above but which, due to the degeneracy of the genetic code, still encode the hCRY2 receptor. Of course, the genetic code is well known in the art. Thus, it would be routine for one skilled in the art to generate such degenerate variants.

In another aspect, the invention provides isolated nucleic acid molecules encoding the hCRY2 polypeptide having an amino acid sequence encoded by the cDNA set forth in SEQ ID NO:1 and by the clone contained in the plasmid deposited as ATCC Deposit No. 97769 on Oct. 22, 1996. In further embodiments, this nucleic acid molecule will encode the mature polypeptide or the full-length polypeptide lacking the N-terminal methionine. The invention further provides an isolated nucleic acid molecule having the nucleotide sequence shown in SEQ ID NO:1 or the nucleotide sequence of the hCRY2 receptor cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the hCRY2 receptor gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, or 1750 nt in length are also useful according to the present invention, as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1.

Preferred nucleic acid fragments of the present invention include nucleic acid molecules encoding: a polypeptide comprising the hCRY2 receptor extracellular domain (predicted to constitute amino acid residues from about 1 to about 492 in SEQ ID NO:2); a polypeptide comprising the hCRY2 receptor transmembrane domain (predicted to constitute amino acid residues from about 493 to about 505 in SEQ ID NO:2); a polypeptide comprising the hCRY2 receptor intracellular domain (predicted to constitute amino acid residues from about 506 to about 571 in SEQ ID NO:2); and a polypeptide comprising the hCRY2 receptor extracellular and intracellular domains with all or part of the transmembrane domain deleted. As above with the leader sequence, the amino acid residues constituting the hCRY2 receptor extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the present invention also include nucleic acid molecules encoding epitope-bearing portions of the hCRY2 receptor protein. In particular, such nucleic acid fragments of the present invention include nucleic acid molecules encoding: a polypeptide comprising amino acid residues from about 8 to about 17 in SEQ ID NO:2; a polypeptide comprising amino acid residues from about 23 to about 30 in SEQ ID NO:2; a polypeptide comprising amino acid residues from about 55 to about 70 in SEQ ID NO:2; a polypeptide comprising amino acid residues from about 74 to about 81 in SEQ ID NO:2; a polypeptide comprising amino acid residues from about 136 to about 147 in SEQ ID NO:2; a polypeptide comprising amino acid residues from about 156 to about 165 in SEQ ID NO:2; a polypeptide comprising amino acid residues from about 231 to about 239 in SEQ ID NO:2; a polypeptide comprising amino acid residues from about 271 to about 279 in SEQ ID NO:2; a polypeptide comprising amino acid residues from about 298 to about 309 in SEQ ID NO:2; a polypeptide comprising amino acid residues from about 316 to about 324 in SEQ ID NO:2; a polypeptide comprising amino acid residues from about 328 to about 334 in SEQ ID NO:2; a polypeptide comprising amino acid residues from about 415 to about 426 in SEQ ID NO:2; and a polypeptide comprising amino acid residues from about 512 to about 519 in SEQ ID NO:2. It is believed that the above polypeptide fragments are antigenic regions of the hCRY2 receptor. Methods for determining other such epitope-bearing portions of the hCRY2 protein are described in detail below.

In addition, the present inventors have identified nucleic acid molecules having nucleotide sequences related to extensive portion of SEQ ID NO:1 which have been determined from the following related cDNA clones: HFCAD18R (SEQ ID NO:17); HDPFZ96R (SEQ ID NO:18); BBNAG83R (SEQ ID NO:19); and HJBAZ81R (SEQ ID NO:20). HFCAD18R (SEQ ID NO:17) is related to nucleotides 1372 to 1661 of SEQ ID NO:1. HDPFZ96R (SEQ ID NO:18) is related to nucleotides 611 to 712 of SEQ ID NO:1. HBNAG83R (SEQ ID NO:19) is related to nucleotides 3546 to 3691 of SEQ ID NO:1. HJBAZ81R (SEQ ID NO:20) is related to nucleotides 2460 to 2600 of SEQ ID NO:1.

The sequence of a public EST, having GenBank Accession No. AA338421, related to a portion of SEQ ID NO:1 is shown in SEQ ID NO:21. This public EST contains a region of 290 nucleotides that are related to nucleotides 1260–1549 of SEQ ID NO:1.

The sequence of another public EST, having GenBank Accession No. AA297444, related to a portion of SEQ ID NO:1 is shown in SEQ ID NO:22. This public EST contains a region of 210 nucleotides that are related to nucleotides 1102–1311 of SEQ ID NO:1.

In another aspect, the invention provides an isolated nucleic acid molecule comprising a polynucleotide which hybridizes under stringent hybridization conditions to a portion of the polynucleotide in a nucleic acid molecule of the invention described above, for instance, the full-length cDNA set forth in SEQ ID NO:1 or the cDNA clone contained in ATCC Deposit 97769. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1).

Of course, a polynucleotide which hybridizes only to a poly A sequence (such as the 3' terminal poly(A) tract of the hCRY2 receptor cDNA shown in SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a hCRY2 polypeptide may include, but are not limited to those encoding the amino acid sequence of the mature polypeptide, by itself; the coding sequence for the mature polypeptide and additional sequences, such as those encoding the about 22 amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, MRNA processing, including splicing and polyadenylation signals, for example—ribosome binding and stability of MRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., Proc. Natl. Acad Sci. USA 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include the hCRY2 receptor fused to the maltose binding protein sequence (see Examples 1 and 2), or to Fc at the N- or C-terminus.

The present invention further relates to variants of the nucleic acid molecules of the present invention, which encode portions, analogs or derivatives of the hCRY2 receptor. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the hCRY2 receptor or portions thereof Also especially preferred in this regard are conservative substitutions.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the complete amino acid sequence in SEQ ID NO:2; (b) a nucleotide sequence encoding the polypeptide having the complete amino acid sequence in SEQ ID NO:2 except for the N-terminal methionine (amino acid residues -21 to 571 in SEQ ID NO:2); (c) a nucleotide sequence encoding the polypeptide having the amino acid sequence at positions from about 1 to about 571 in SEQ ID NO:2; (d) a nucleotide sequence encoding the polypeptide having the amino acid sequence at positions from about 191 to about 571 in SEQ ID NO:2; (e) a nucleotide sequence encoding the hCRY2 polypeptide having the amino acid sequence encoded by the cDNA clone contained in ATCC Deposit No. 97769; (f) a nucleotide sequence encoding the mature hCRY2 receptor having the amino acid sequence encoded by the cDNA clone contained in ATCC Deposit No. 97769; (g) a nucleotide sequence encoding the hCRY2 receptor extracellular domain; (h) a nucleotide sequence encoding the hCRY2 receptor transmembrane domain; (i) a nucleotide sequence encoding the hCRY2 receptor intracellular domain; (j) a nucleotide sequence encoding the hCRY2 receptor extracellular and intracellular domains with all or part of the transmembrane domain deleted; and (k) a nucleotide sequence complementary to any of the nucleotide sequences in (a), (b), (c), (d), (e), (f), (g), (h), (i), or ).

By a polynucleotide having a nucleotide sequence at least, for example, 95% "identical" to a reference nucleotide sequence encoding a hCRY2 polypeptide is intended that the nucleotide sequence of the polynucleotide is identical to the reference sequence except that the polynucleotide sequence may include up to five point mutations per each 100 nucleotides of the reference nucleotide sequence encoding the hCRY2 receptor. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 990% identical to, for instance, the nucleotide sequence shown in SEQ ID NO:1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advaces in Applied Mathematics* 2: 482489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 990/0 identical to the nucleic acid sequence shown in SEQ ID NO:1 or to the nucleic acid sequence of the deposited cDNA, irrespective of whether they encode a polypeptide having hCRY2 receptor activity. This is because even where a particular nucleic acid molecule does not encode a polypeptide having hCRY2 receptor activity, one of skill in the art would still know how to use the nucleic acid molecule, for instance, as a hybridization probe or a polymerase chain reaction (PCR) primer. Uses of the nucleic acid molecules of the present invention that do not encode a polypeptide having hCRY2 receptor activity include, inter alia, (1) isolating the hCRY2 receptor gene or allelic variants thereof in a cDNA library; (2) in situ hybridization (e.g., "FISH") to metaphase chromosomal spreads to provide precise chromosomal location of the hCRY2 receptor gene, as described in Verma et al., *Human Chromosomes: A Manual of Basic Techniques*, Pergamon Press, New York (1988); and (3) Northern Blot analysis for detecting hCRY2 receptor mRNA expression in specific tissues.

Preferred, however, are nucleic acid molecules having sequences at least 95%, 96%, 97%, 98% or 99% identical to the nucleic acid sequence shown in SEQ ID NO:1 or to the nucleic acid sequence of the deposited cDNA which do, in fact, encode a polypeptide having hCRY2 receptor activity.

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNA or the nucleic acid sequence shown in SEQ ID NO:1 will encode a polypeptide "having hCRY2 receptor activity." It will be further recognized in the art that, for such nucleic acid molecules that are not degenerate variants, a reasonable number will also encode a polypeptide having hCRY2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bovie, J. U. et al., "Deciphering the Message in Protein Sequences: Tolerance to Amino Acid Substitutions," Science 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of hCRY2 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofiolate reductase or neomycin resistance for eukaryotic cell culture and tetracycline or ampicillin resistance genes for culturing in *E. coli* and other bacteria Representative examples of appropriate heterologous hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAB-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The hCRY2 receptor can be recovered and purified from recombinant cell cultures by well-known methods, including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

hCRY2 Polypeptides and Fragments

The invention further provides an isolated hCRY2 polypeptide having the amino acid sequence encoded by the deposited cDNA, or the amino acid sequence in SEQ ID NO:2, or a peptide or polypeptide comprising a portion of the above polypeptides.

It will be recognized in the art that some amino acid sequences of the hCRY2 receptor can be varied without significant effect of the structure or function of the protein. If such differences in sequence are contemplated, it should be remembered that there will be critical areas on the protein which determine activity.

Thus, the invention further includes variations of the hCRY2 receptor which show substantial hCRY2 receptor activity or which include regions of hCRY2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the hCRY2 protein. The prevention of aggregation is highly desirable. Aggregation of proteins not only results in a loss of activity but can also be problematic when preparing pharmaceutical formulations, because they can be immunogenic (Pinckard et al., *Clin. Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al. (*Nature* 361:266–268 (1993)) describes certain mutations resulting in selective binding of TNF-α to only one of the two known types of TNF receptors. Thus, the hCRY2 receptor of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given hCRY2 polypeptide will not be more than 50, 40, 30, 20, 10, 5, or 3.

Amino acids in the hCRY2 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced or contained in a recombinant host cell is considered "isolated" for the purposes of the present invention. Also intended as "isolated" is a polypeptide that has been purified, partially or substantially, from a recombinant host or a native source. For example, a recombinantly produced version of the hCRY2 receptor can be substantially purified by the one-step method described in Smith and Johnson, *Gene* 67:31–40 (1988).

The polypeptides of the present invention also include the complete polypeptide encoded by the deposited cDNA; the mature polypeptide encoded by the deposited the cDNA; amino acid residues −22 to 571 of SEQ ID NO:2; amino acid residues −21 to 571 of SEQ ID NO:2; amino acid residues 1 to 571 of SEQ ID NO:2; amino acid residues 191 to 571 of SEQ ID NO:2; the extracellular domain; the transmembrane domain; and the intracellular domain, as well as polypeptides which are at least .95% identical, more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a hCRY2 polypeptide is intended that the amino acid sequence of the polypeptide is identical to the reference sequence except that the polypeptide sequence may include up to five amino acid alterations per each 100 amino acids of the reference amino acid of the hCRY2 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to those described above can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

It is believed that the hCRY2 receptor is involved in the circadian regulation of mammalian physiology. Thus, ligands which bind to the hCRY2 receptor would be useful in treating patients with primary sleep disorders (e.g., disorders with no apparent cause). Ligands which bind to the hCRY2 receptor would also be useful in treating patients with sleep disorders caused by odd working hours (e.g., among patients who work during the night or who work rotating shifts).

It is also believed that the hCRY2 receptor is involved in mediating repair of damage to DNA, proteins, cells or tissue (e.g., skin) caused by ultraviolet light. Thus, ligands which bind to the hCRY2 receptor would be useful in treating patients suffering from UV damage.

As indicated below, the hCRY2 polypeptides of the present invention can be used to generate antibodies. Such antibodies can be used to investigate the expression, regulation, and ligand binding properties of the hCRY2 receptor.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A, Antibodies that react with predetermined sites on protein, *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Non-limiting examples of antigenic polypeptides or peptides that can be used to generate hCRY2 receptor-specific antibodies include: a polypeptide comprising amino acid residues from about 8 to about 17 in SEQ ID NO:2; a polypeptide comprising amino acid residues from about 23 to about 30 in SEQ ID NO:2; a polypeptide comprising amino acid residues from about 55 to about 70 in SEQ ID NO:2; a polypeptide comprising amino acid residues from about 74 to about 81 in SEQ ID NO:2; a polypeptide comprising amino acid residues from about 136 to about 147 in SEQ ID NO:2; a polypeptide comprising amino acid residues from about 156 to about 165 in SEQ ID NO:2; a polypeptide comprising amino acid residues from about 231 to about 239 in SEQ ID NO:2; a polypeptide comprising amino acid residues from about 271 to about 279 in SEQ ID NO:2; a polypeptide comprising amino acid residues from about 298 to about 309 in SEQ ID NO:2; a polypeptide comprising amino acid residues from about 316 to about 324 in SEQ ID NO:2; a polypeptide comprising amino acid residues from about 328 to about 334 in SEQ ID NO:2; a polypeptide comprising amino acid residues from about 415 to about 426 in SEQ ID NO:2; and a polypeptide comprising amino acid residues from about 512 to about 519 in SEQ ID NO:2. As indicated above, the inventors have determined that the above polypeptide fragments are antigenic regions of the hCRY2 receptor protein.

The epitope-bearing peptides and polypeptides of the invention may be produced by any conventional means. Houghten, R. A., General method for the rapid solid-phase synthesis of large numbers of peptides: Specificity of antigen-antibody interaction at the level of individual amino acids, *Proc. Natl. Acad Sci. USA* 82:5131–5135 (1985). This "Simultaneous Multiple Peptide Synthesis (SMPS)" process is further described in U.S. Pat. No. 4,631,211 to Houghten et al. (1986).

As one of skill in the art will appreciate, hCRY2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian imnmunoglobulins (EPA 394,827; Traunecker et al., *Nature* 331:84–86 (1988)).

Fusion proteins that have a disulfide-linked dimeric structure due to the IgG part can also be more efficient in binding and neutralizing other molecules than the monomeric hCRY2 protein or protein fragment alone (Fountoulakis et al., *J. Biochem.* 270:3958–3964 (1995)).

Detection of hCRY2 Gene Expression

The expression level of the hCRY2 gene can be readily assayed by one of ordinary skill in the art. By "assaying the expression level of the gene encoding the hCRY2 protein" is intended qualitatively or quantitatively measuring or estimating the level of the hCRY2 protein or the level of the mRNA encoding the hCRY2 receptor in a biological sample (e.g., by determining or estimating absolute protein level or mRNA level).

By "biological sample" is intended any biological sample obtained from an individual, cell line, tissue culture, or other source which contains hCRY2 protein or mRNA. Such tissues include cerebellum, retina, breast, pituitary, heart, placenta, lung, skeletal muscle, kidney, and pancreas. Biological samples include mammalian tissues which contain hCRY2 protein. Preferred mammals include monkeys, apes, cats, dogs, cows, pigs, horses, rabbits, and humans. Particularly preferred are humans.

Total cellular RNA can be isolated from a biological sample using the single-step guanidinium-thiocyanate-phenol-chloroform method described in Chomcynski and Sacchi (*Anal. Biochem.* 162:156–159 (1987)). Levels of mRNA encoding the hCRY2 receptor are then assayed using any appropriate method. These include Northern blot analysis (Harada et al, *Cell* 63:303–312 (1990)), S1 nuclease mapping (Harada et al., *Cell* 63:303–312 (1990)), the polymerase chain reaction (PCR), reverse transcription in combination with the polymerase chain reaction (RT-PCR) (Fujita et al., *Cell* 49:35–36 (1990)), and reverse transcription in combination with the ligase chain reaction (RT-LCR).

As discussed supra, assaying hCRY2 protein levels in a biological sample can occur using antibody-based techniques. For example, hCRY2 protein expression in tissues can be studied with classical immunohistological methods (Jalkanen, M. et al, *J. Cell Biol.* 101:976–985 (1985); Jalkanen, M. et al., *J. Cell. Biol.* 105: 3087–3096 (1987)). Other antibody-based methods useful for detecting hCRY2 receptor gene expression include immunoassays, such as the enzyme linked immunosorbent assay (ELISA) and the radioimmunoassay (RIA). Suitable labels are known in the art and include enzyme labels, such as glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a hCRY2 receptor gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data Such data are found, for example, in V. McKusick, Mendelian Inheritance In Man, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLE 1

Cloning the Human Photoreceptor

The cDNA clone (R1931) for the human photolyase homolog (Adams, M. D. et al, *Nature* 377:3–174 (1995)), carrying the 3' terminal 1038 bp of the open reading frame gene, was obtained from R. K. Wilson (Washington University, St. Louis). The 5' terminal part of the gene was obtained using the 5' RACE System for Rapid Amplification of cDNA ends (GibcoBRL, Gaithersburg, Md., USA) as described by the manufacturer and using mRNA from the T093 human fibroblast cell line. The amplified product was digested with NcoI and Hind III and cloned into the Nco I/Hind III sites of the baculovirus expression vector p2Bac (Invitrogen, San Diego, Calif., USA) and the *E. coli* expression vector pKK233-2 (Pharmacia, Uppsala, Sweden). Sequence of the gene was confirmed by double strand DNA sequencing using the Sequenase DNA sequencing kit (US Biochemical, Arlington, Ill., USA) and was in complete agreement with the previously published sequence (Todo, T. et al., *Science* 272:109–112 (1996)). A maltose binding protein (MBP) fusion construct was made by inserting the Bgl II/Hind III fragment carrying the entire photolyase homolog coding region into the H I/Hind III site of the MBP expression vector pMal-c2 (NEB, Beverly, Mass., USA). This construct was named pDH1996-1.

The sequence of the second homolog was first identified by searching a database containing approximately 1 million human ESTs, which was generated using high throughput automated DNA sequence analysis of randomly selected human cDNA clones (Adams, M. D. et al., *Nature* 377:3–174 (1995); Adams, M. D. et al., *Nature* 355:632–634 (1992); and Adams, M. D. et al., *Science* 252:1651–1656 (1991)). Sequence homology comparisons of each EST were performed against the GenBank database using the blastn and tblastn algorithms (Altschul, S. F. et al., *J. Mol. Biol.* 215:403–410 (1990)). A specific homology search using the known human photolyase homolog 1 amino acid sequence against this human EST database revealed two ESTs (HGS6392 and HGS47815). Both were from a human fetal brain cDNA library, with greater than 84% homology to the first homolog. The two ESTs are identical except HGS47815 is 183 bp longer at the 5' end. HGS47815 contains 3035 bp and the sequence comparison suggested that it is missing approximately 1 kb of the putative photolyase homolog at the 5' end. Using this clone as a probe, a hybridization screening was conducted through the human fetal brain cDNA library from which HGS6392 and HGS47815 were initially discovered. From this screening, a positive clone (SO5), which was 466 bp longer than HGS47815, was identified.

The gene identified previously (Adams et al. (1995); Todo et al. (1996) has been designated hCRY1. In the present specification, the human photolyase homolog genes are referred to as hCRY1 and hCRY2 and the corresponding gene products are referred to at hCRY1 and hCRY2, respectively. These names are in compliance with the nomenclature for blue-light photoreceptors (i.e., cryptochromes) in plants (Short, T. W et al., *Ann. Rev. Plant. Physiol. Plant Mol. Biol.* 45:143–171 (1994)). The gene of the present invention has been designated hCRY2.

The hCRY2 gene was originally identified in a human fetal brain cDNA library and was found to be expressed in fibroblasts as well. Further, the hCRY2 gene was detected in human cDNA libraries prepared from fetal brain, synovial sarcoma, resting T-cel, infant brain, cerebellum, endometrial tumor, testes tumor, adult retina, chondrosarcoma, breast, and pituitary. Compared to hCRY1, hCRY2 occurred at lower frequency in the human cDNA database in all tissues tested.

To obtain the entire 5' terminal part of the hCRY2 gene, the RACE PCR procedure was used. Briefly, a specific primer for the 3' end of the gene, 5'-GGGCTCT-GCCACAGGGTGACTGAGGTC-3' (SEQ ID NO:7), was used for first stand cDNA synthesis. First round of PCR amplification for the 5' terminal part of the hCRY2 gene was carried out using a gene specific primer, 5'-AATACCCGGACCCCGCTC-3' (SEQ ID NO:8), at the 3' end of the gene and a degenerative primer at the 5' end as described by the manufacturer. This was followed by a second round of amplification using another gene specific primer, 5' CAGGTCCCACAGGCGGTA-3' (SEQ ID NO:9) at the 3' end of the gene and another degenerative primer at the 5' end. Sequence comparison of the open reading frame of the amplified product to the first photolyase homolog confirmed that the 5' end of the gene had been cloned.

A MBP fusion of the SO5 clone was constructed by ligating an EcoRI/BglII fragment containing the entire open reading frame of SO5 into the EcoRI/HI site of pMal-c2. This construct, which encodes the carboxy terminal 381 amino acids of the hCRY2 protein (amino acid residues 191–571 in SEQ ID NO:2), was named pDHI996-2.

Large scale sequencing of expression sequence tagged (EST) cDNAs revealed a clone with homology to the microbial photolyase genes. This clone was designated a photolyase isolog since there is no convincing evidence that humans have a photolyase which can repair cyclobutane pyrimidine dimers (Adams, M. D. et al., *Nature* 377:3–174 (1995)). Independently, Todo et al. cloned and sequenced the gene for the apoenzyme of the newly discovered (6-4) photolyase from *D. melanogaster* (Todo, T. et al., *Science* 272:109–112 (1996)). It was found that the (6-4) photolyase has high degree of homology with the photolyase/blue-light photoreceptor family of proteins (Ahmad, M. et al., *Nature* 366:162–166 (1993); Malhotra,K. et al., *Biochemistry* 34:6892–6899 (1995)), including the human photolyase isolog. In fact, when the entire cDNA of the human photolyase isolog was isolated and sequenced, it revealed an astonishing 48% sequence identity with the *D. melanogaster* (6-4) photolyase (Todo, T. et al., *Science* 272:109–112 (1996)).

Sequence comparison of the hCRY1 and hCRY2 proteins, along with a representative member of a type I (microbial) class photolyase, the blue-light photoreceptor gene HY4 of *A. thaliana*, and the (6-4) photolyase of *D. melanogaster*, are shown in FIG. 4. hCRY1 and hCRY2 exhibit 65% sequence identity at the nucleotide level and 74% sequence identity at the amino acid level. hCRY2 also shows high degree of sequence homology to *D. melanogaster* (6-4) photolyase with a 51% sequence identity over the entire length.

Aside from the high degree of sequence homology between hCRY1 and hCRY2, the most noteworthy feature of the sequences of these proteins is the complete divergence over the carboxy-terminal 80 amino acids. A similar divergence has been found between the two *A. thaliana* blue-light photoreceptors (Ahmad, M. et al., *Plant Molec. Biol.* 30:851–861 (1996)). It is believed that this "tail" region of the *A. thaliana* photoreceptor interacts with an effector molecule (Lin, C. et al., *Proc. Natl. Acad Sci. USA* 98:6389–6393 (1995)). It is also believed that the hCRY1 and hCRY2 proteins also interact with downstream targets.

EXAMPLE 2

Figure 5:
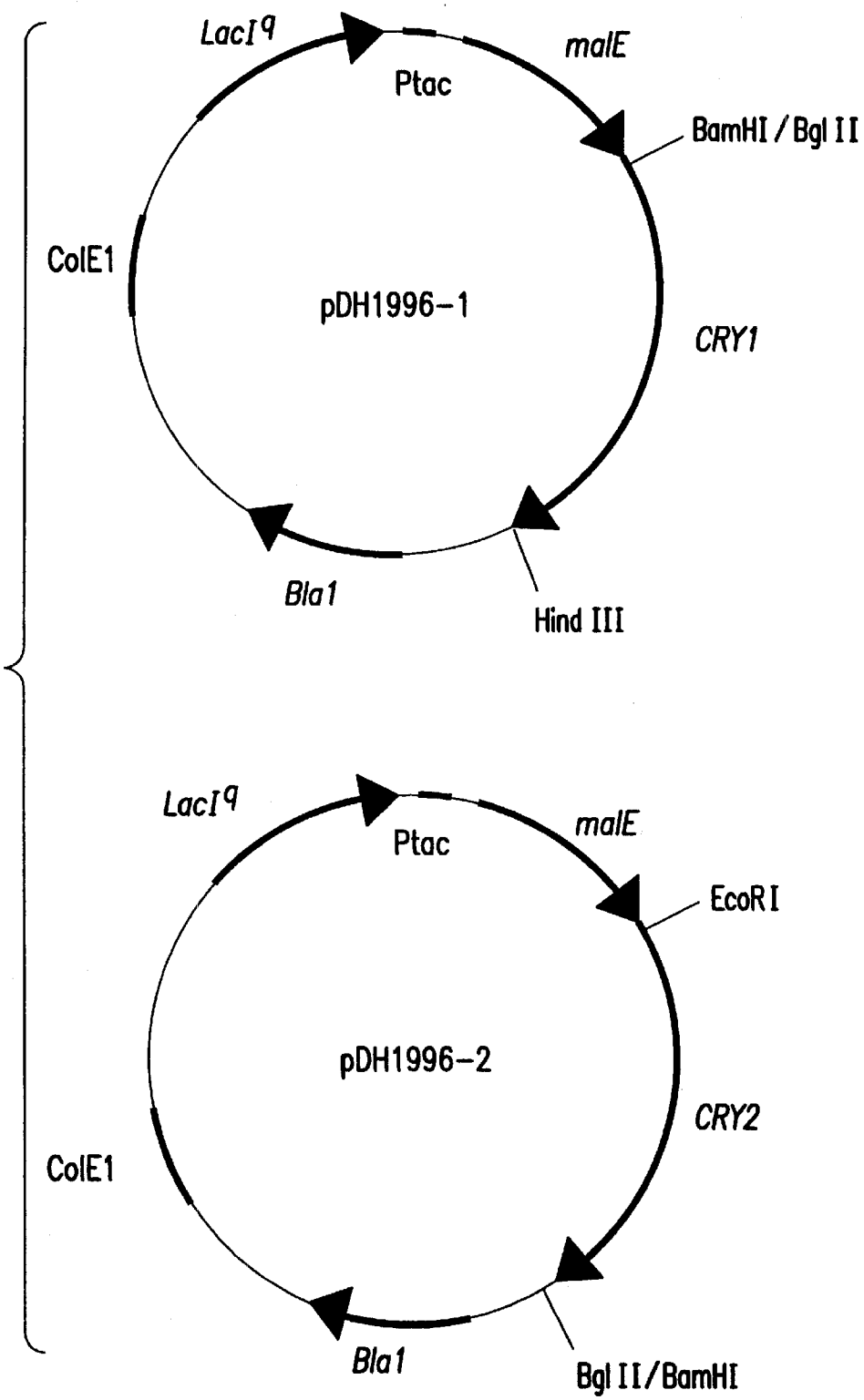
FIG. 5 shows the maps of plasmids pDH1996-1 and pDH1996-2, which were used to express hCRY1 and hCRY2, respectively, as maltose binding fusion proteins. PDH1996-1 contains the hCRY1 cDNA pDH1996-2 contains the hCRY2 cDNA The arrows indicate the length and direction of transcription of the maltose binding protein (malE), blal, and photoreceptor genes.

Purification of Recombinant Human CRY Proteins hCRY1 and hCRY2 proteins were expressed as MBP fusion proteins, using the MBP fusion vector pMal-c2 FIG. 5), in DR153 *E. coli* cells. The hCRY1 construct was called pDH1996-1. The hCRY2 construct was called pDH1996-2. As discussed supra, pDH1996-2 contains the carboxy terminal 381 amino acids (amino acid residues 191–571 in SEQ ID NO:2). Oligonucleotide primers were used to amplify the hCRY2 sequence. The 5' primer sequence was 5'-CGCGAATTCCTCCCTGGAGGAGCTGGG-3' (SEQ ID NO:10), which contains the underlined EcoR I restriction site followed by 19 bases corresponding to nucleotides 635654 in the sequence set forth in SEQ ID NO:1. The 3' primer sequence was 5'-GCGAGATCTTCAGGCATCC-TTGCTCGG-3(SEQ ID NO:11), which contains the underlined Bgl II restriction site, followed by 18 bases reverse and complementary to nucleotides 1825–1842 in the sequence set forth in SEQ ID NO:1.

A longer MBP-hCRY2 fusion protein, containing amino acid residues -15 to 571 of the sequence set forth in SEQ ID NO:2, was expressed in DR153 cells using the pMal-c2 vector. Oligonucleotide primers were used to amplify the longer hCRY2 sequence. The 5' primer sequence was 5'-GCGGATACGCGGCAGCTGTGGCCCCG-3' (SEQ ID NO:12), which contains the underlined EcoR V restriction site followed by 18 bases corresponding to nucleotides 22–39 in the sequence set forth in SEQ ID NO:1. The 3' primer sequence was 5'-GCGAACTTTCAGGCATCCTT-GCTCGG-3' (SEQ ID NO:13), which contains the underlined Hind III restriction site, followed by 18 bases reverse and complementary to nucleotides 1825–1842 in the sequence set forth in SEQ ID NO:1. This amplified fragment was digested with EcoR V and Hind III prior to ligation into the pMal-c2 vector (after digestion of the vector with Xmn I and Hind III).

Expressed proteins were purified by affinity chromatography on amylase resin (Malhotra, K. et al., *Biochemistry* 34:6892–6899 (1995)). Since the possibility exists that fusion with MBP may interfere with enzymatic function, a MBP fusion form of the *D. melanogaster* (6-4) photolyase (Todo, T. et al., *6Science* 272: 109–112 (1996)) was used as a control. As discussed supra, the (6-4) photolyase is highly homologous to the hCRY1 and hCRY2 photoreceptors and was prepared and purified as were the hCRY1 and hCRY2 proteins.

EXAMPLE 3

Spectroscopic Properties of hCRY1 and hCRY2

All photolyases and blue-light photoreceptors that have been characterized to date contain FAD and a second chromophore, which is a folate in most organisms. In a few species which can synthesize deazaflavin, the second photolyase chromophore is deazariboflavin (Eker, AP. et al., *J. Biol. Chem.* 265:8009–8015 (1990); Malhotra, K. et al., *Biochemistry* 34: 6892–6899 (1995)). hCRY1 and hCRY2 were assayed for the presence of chromophores. The absorption spectra of the purified hCRY1 and hCRY2 proteins were recorded with a Hewlett-Packard Model 8451A spectrophotometer and the fluorescence spectra of the chromophores were measured at 22° C. in a Shimadzu RF5000 U Spectrofluorometer.

Figure 6A:
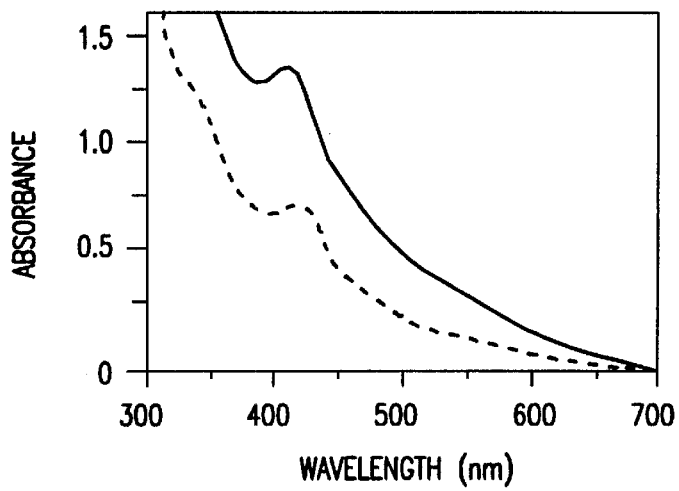
FIG. 6 shows the absorption and fluorescence spectra of hCRY1 and hCRY2 MBP fusion proteins. The dashed line represents the spectra of hCRY1 and the solid line represents the spectra of hCRY2. (A) Absorption spectra. (B) Fluorescence excitation and emission spectra of the hCRY1 and hCRY2 chromophores at pH 2. Fluorescence excitation spectra were recorded by monitoring emission at 520 nm. Fluorescence emission spectra were recorded by using excitation at 450 nm. (C) Fluorescence excitation and emission spectra of hCRY1 and hCRY2 chromophores at pH 10. Fluorescence excitation spectra were recorded by monitoring emission at 470 nm. Fluorescence emission spectra were recorded by using 380 nm excitation.

The absorption spectra of the MBP fusion forms of hCRY1 and hCRY2 (amino acids residues 191–571 in SEQ ID NO:2) are shown in FIG. 6A Both proteins exhibited a distinct 420 nm peak with residual absorption extending all the way to 700 nm. The absorption spectra were almost identical to the absorption spectra of the cyclobutane pyrimidine dimer photolyase (Kim, S. T. et al., *Mutation Res.* 363:97–104 (1996)) and the (6-4) photolyase (data not shown) from *D. melanogaster*.

Figure 6B:
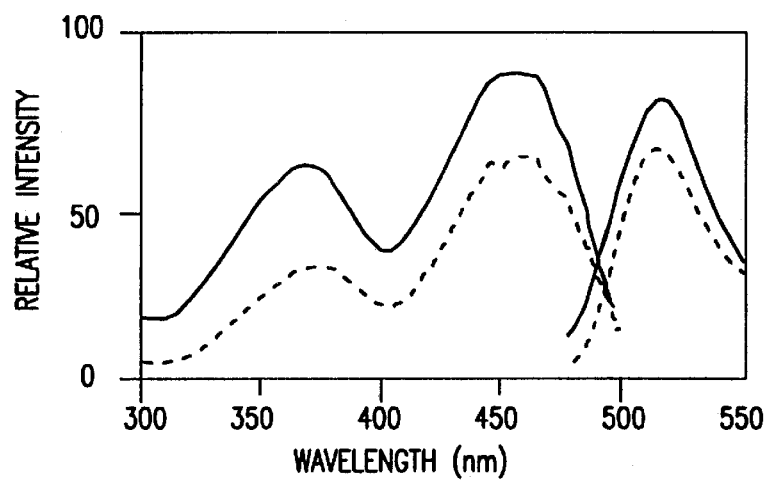

It has been demonstrated that the *D. melanogaster* T< >T photolyase contained FAD and folate as chromophores (Kim, S. T. et al., Mutation Res. 363:97–104 (1996)). Hence, it was reasoned that hCRY1 and hCRY2 may also contain these cofactors. A simple assay revealed that this is indeed the case. hCRY1 and hCRY2 were denatured by heating for 10 minutes at 65° C. in 0.1 M HCL and 0.8% SDS. Following centrifugation to remove the protein precipitate, excitation and emission fluorescence spectra were recorded. FIG. 6B shows a diagnostic flavin fluorescence spectrum. It was concluded that both hCRY1 and hCRY2 contain flavin. Furthermore, upon increasing the pH to 10 by addition of NaOH, the flavin fluorescence was severely quenched, further confirming the cofactor as FAD (Faeder, E. J., *Anal. Biochem.* 53:332–336 (1973)).

Figure 6C:
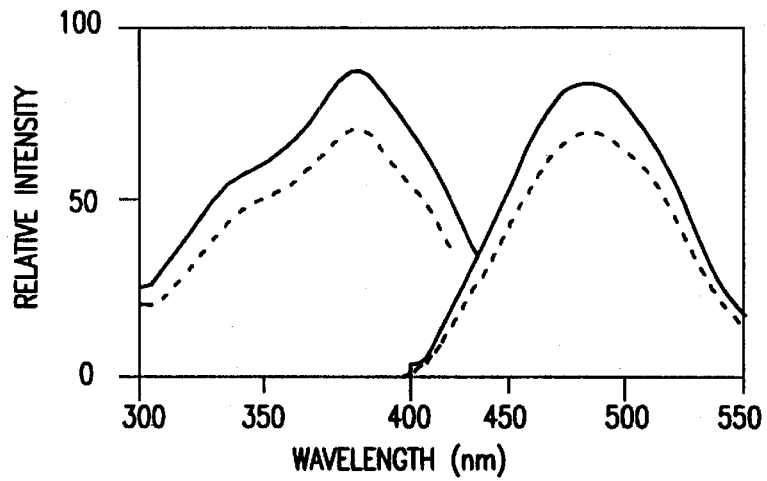

Alkaline pH had another notable effect on the fluorescence spectrum: a new species with an excitation maximum at 380 and emission maximum at 470 appeared (FIG. 6C). This behavior is typical of reduced pterin, which is non-fluorescent but is converted to highly fluorescent oxidized pterin upon incubation in alkaline solutions (Johnson, J. L. et al., *Proc. Natl. Acad Sci. USA* 85:2046–2050 (1988)). Furthermore, the excitation and emission spectra of the second chromophore are identical to that of the *D. melanogaster* T< >T photolyase, which was shown to be a folate by TLC analysis with appropriate standards (Kim, S. T. et al., *Mutation Res.* 363:97–104 (1996)). Thus, it was concluded that hCRY1 and hCRY2, like other members of the photolyase/photoreceptor family, contain FAD and a pterin as the two chromophore/cofactors.

EXAMPLE 4

Photolyase Activity Assay

In a photolyase assay, the restoration of the susceptibility to cleavage of the TTAA sequence by the MseI restriction endonuclease was measured in a DNA fragment where the TT is either in the form of a cyclobutane thymine dimer (T< >T) or (6-4) photoproduct (Malhotra, K. et al., *Biochemistry* 34:6892–6899 (1995); Kim, S. T. et al., *Photochem. Photobiol.* 63:292–295 (1996)). A 54 mer oligonucleotide duplex, and a 49 mer oligonucleotide duplex, containing a centrally located T< >T and T[6-4]T, respectively, were prepared as described previously (Smith, C. A, *J. Biol. Chems.* 268:11143–11151 (1993)) and were kindly provided by Dr. J. S. Taylor (Washington University).

In the photoreactivation assay, hCRY1 and hCRY 2 (amino acids residues 191–571 in SEQ ID NO:2) proteins (40 nM) were mixed with 0.5 nNM substrate in a 50 µl reaction containing 50 mM Tris pH 7.4, 100 mM NaCl, 6 mM dithiothreitol, 2 mM EDTA, 5 µg bovine serum albumin and 5% glycerol. The mixture was incubated in the dark at room temperature for 10 minutes and then exposed to photoreactivating light ($\lambda_{max}$=366 nm), at 4° C. for 1 hour, from a Sylvania black light (Model B-100) at a fluence rate of 2 milliwatts/cm2. The DNA was then extracted with phenol/chloroform, precipitated with ethanol, resuspended in restriction enzyme buffer and digested with 8 units of MseI for 1 hour. The reaction products were electrophoresed on a 8% denaturing gel and the level of digested (repaired) DNA was determined by a Phospholmager (Molecular Dynamics Inc.). For the (6-4) photoproduct, the level of 21mer detected indicated the extent of repair. For the T< >T substrate, the level of 19mer detected indicated the extent of repair.

The spectroscopic properties of hCRY1 and hCRY2 (supra) were consistent with these proteins being a Pyr< >Pyr photolyase, a (6-4) photolyase, or a photoreceptor. To differentiate between these possibilities, the recombinant proteins were tested for repair activity. *E. coli* photolyase repaired a T< >T photoproduct. 54% of the T< >T substrate was repaired. However, both CRY1 and hCRY2 failed to repair the T< >T photoproduct.

*D. melmogaster* (6-4) photolyase repaired a T[6-4]T photoproduct. 48% of the photoproduct was repaired. In contrast, both CRY1 and hCRY2 failed to repair the T[6-4]T photoproduct. After conducting the repair experiments were under a variety of conditions (higher protein concentration and higher dose of photoreactivating light), it was concluded that hCRY1 and hCRY2 cannot have more than 0.1% of the photolyase activities detected with bona fide photolyases. Thus, it was concluded that the recombinant photolyase homologs do not have photolyase activity.

Even though these data strongly suggest that hCRY1 and hCRY2 are not photolyases, it is conceivable that the proteins expressed in heterologous system were somewhat misfolded or lacked a posttranslational modification necessary for activity. Hence, the natural sources were tested for activity. Cell-free extracts from fibroblasts (T093), which expressed hCRY1 and hCRY2 (as revealed by primer extension (for both hCRY1 and hCRY2) and immunoblotting (for hCRY1 only), failed to show any (6-4) photolyase activity.

To ascertain whether this lack of activity was due to inhibition by other proteins known to exist in cell-free extracts which bind to (6-4) photoproduct (Chu, G. et al., *Science* 242:564–567 (1988); Ghosh, R. et al., *Proc. Natl. Acad Sci. USA* 93:6918–6923 (1996); Wakasugi, M. et al., *Nucl. Acids Res.* 24:1099–1104 (1996)), Drosophila (6-4) photolyase was mixed with the fibroblast cell free extract and this mixture was assayed for photoreactivation activity using a T(6-4)T substrate. Assays with human cell free extract (infra) were performed in a similar manner as describe supra, except that 50 µg of CFE was used in the reaction.

In the absence of cell-free extract, Drosophila (6-4) photolyase repaired 38% of the T(6-4) substrate. In the presence of cell-free extract, Drosophila (6-4) photolyase repaired 29% of the substrate. This level of inhibition cannot explain the total lack of photolyase activity in the cell-free extract, which was assayed under a variety of conditions.

Finally, hCRY1 purified from a baculovirus/insect cell expression system also failed to show any photolyase activity (data not shown). Thus, hCRY1 and hCRY2 do not appear to possess a photolyase activity.

The longer form of the MBP-hCRY2 fusion protein, containing amino acids −15 to 571 in SEQ ID NO:2, displayed spectral properties similar to those of the MBP-hCRY2 fusion protein that contained only amino acid residues 191–571. Like the shorter MBP-hCRY2 fusion protein, the longer MBP-hCRY2 fusion protein failed to exhibit photolyase activity.

Many attempts from several labs to detect and isolate photolyases from human cells have failed, leading to a near-consensus in the field that humans do not have photolyase (Ley, R. D., Proc. Natl. Acad Sci. USA 98:4337 (1993); Li, Y. F. et al., Proc. Natl. Acad. Sci. USA 90:43894393 (1993); Kato, T. et al., Nucl. Acids. Res. 22:4119-4124 (1994)). However, the recent discovery of a photolyase for (6-4) photoproducts, and the finding that it belongs in the photolyase/photoreceptor family of proteins (Todo, T. et al., Nature 361:371–374 (1996)), raised the interesting possibility that humans might have a (6-4) photolyase. Furthermore, a human homolog, with 48% sequence identity with D. melmogaster (6-4) photolyase, was identified (Todo et al., (1996)). The encoded protein could have been the elusive cyclobutane pyrimidine dimer photolyase described by Sutherland et al., (Proc. Natl. Acad. Sci. USA 92:9732–9736 (1996)), a (6-4) photolyase which had not been searched for in humans in a systematic way, or a photoreceptor. This present work was undertaken to differentiate between these possibilities.

The results of the present work clearly show that the human (6-4) photolyase homolog identified previously (hCRY1) and the new homolog identified herein (hCRY2) are neither (6-4) photolyase nor cyclobutane pyrimidine dimer photolyase. Work with recombinant proteins and human cell free extract showed that the proteins encoded by these two genes neither bind to UV damaged DNA (data not shown) nor repair T< >T or T[6-4]T photoproducts in the absence or presence of light. Thus, one is left with the third alternative, that the proteins encoded by the hCRY1 and hCRY2 genes function as blue-light photoreceptors.

EXAMPLE 5

Cloning and Expression of hCRY2 Protein in a Baculovirus Expression System

In this illustrative example, the plasmid shuttle vector pA2 is used to insert the cloned DNA encoding the complete protein, including its naturally associated secretary signal (leader) sequence, into a baculovirus to express the mature hCRY2 protein, using standard methods as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the Autographa califonica nuclear polyhedrosis virus (AcMNPV) followed by convenient restriction sites such as BamH I and Asp 718. The polyadenylation site of the simian virus 40 ("SV40") is used for efficient polyadenylation. For easy selection of recombinant virus, the plasmid contains the beta-galactosidase gene from E. coli under control of a weak promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39.

The cDNA sequence encoding the full length hCRY2 protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5'-GCG AGATCTCCGCCATCATGGCGGCAACTGTGGCAAC-3' (SEQ ID NO:14) containing the underlined Bgl II restriction enzyme site, an efficient signal for initiation of translation in eukaryotic cells, as described by Kozak, M., J. Mol. Biol. 196:947–950 (1987), followed by 20 bases of the sequence of the complete hCRY2 protein shown in SEQ ID NO:1, beginning with the AUG initiation codon. The 3' primer has the sequence 5'-GCGTCTAGATCAGGCATCCTTGCTC-GG-3' (SEQ ID NO:15) containing the underlined Xba I restriction site, followed by 18 nucleotides reverse and complementary to nucleotides 1825–1842 in SEQ ID NO:1.

The amplified fragment is isolated from a 1% agarose gel using a commercially available kit ("Geneclean," BIO 101 Inc., La Jolla, Calif.). The fragment then is digested with Bgl II and Xba I and again is purified on a 1% agarose gel. This fragment is designated herein "F1".

The pA2 vector is digested with the restriction enzymes BamH I and Xba I and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. E. coli HB 101 or other suitable E. coli hosts such as XL-1 Blue (Stratagene Cloning Systems, La Jolla, Calif.) cells are transformed with the ligation mixture and spread on culture plates. Bacteria are identified that contain the plasmid with the human hCRY2 gene using the PCR method, in which one of the primers that is used to amplify the gene and the second primer is from well within the vector so that only those bacterial colonies containing hCRY2 gene fragment will show amplification of the DNA The sequence of the cloned fragment is confirmed by DNA sequencing. This plasmid is designated herein pBachCRY2.

Five μg of the plasmid pBachCRY2 is co-transfected with 1.0 μg of a commercially available linearized baculovirus DNA ("BaculoGold™ baculovirus DNA", Pharmingen, San Diego, Calif.), using the lipofection method described by Feigner et al, Proc. Natl. Acad Sci. USA 84:7413–7417 (1987). 1 μg of BaculoGold™ virus DNA and 5 μg of the plasmid pBachCRY2 are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours, the transfection solution is removed from the plate and 1 ml of Grace's insect medium supplemented with 10% fetal calf serum is added. The plate is put back into an incubator and cultivation is continued at 27° C. for four days.

After four days, the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later, the supernatants of these culture dishes are harvested and then they are stored at 4° C. The recombinant virus is called V-hCRY2.

To verify the expression of the hCRY2 gene, Sf9 cells are grown in Grace's medium supplemented with 10% heat inactivated FBS. The cells are infected with the recombinant baculovirus V-hCRY2 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

EXAMPLE 6

Cloning and Expression of hCRY2 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofiolate reductase) marker is useful to develop cell lines that carry several hundred or even several thousand copies of the gene of interest. Another useful selection marker is the enzyme glutamine synthase (GS) (Murphy et al., *Biochem. J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, Xbal and Asp718, facilitate the cloning of the gene of interest. The vectors contain in addition the 3' intron, the polyadenylation and termination signal of the rat preproinsulin gene.

EXAMPLE 6(a)

Cloning and Expression in COS Cells

The expression plasmid, phCRY2 HA, is made by cloning a cDNA encoding hCRY2 into the expression vector pcDNAI/Amp or pcDNAHI (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAM contains, in addition, the selectable neomycin marker.

A DNA fragment encoding the hCRY2 is cloned into the polylinker region of the vector so that recombinant protein expression is directed by the CMV promoter. The plasmid construction strategy is as follows. The hCRY2 cDNA of the deposited clone is amplified using primers that contain convenient restriction sites, much as described above for construction of vectors for expression of hCRY2 in *E. coli*. Suitable primers include the following, which are used in this example. The 5' primer, containing the underlined Bgl II site, a Kozak sequence, an AUG start codon and 20 bases of the 5' coding region of the hCRY2 has the following sequence: 5'-GCGAGATCTCCGCCATCATGGCGGCAA-CTGTGGCAAC-3' (SEQ ID NO:14). The 3' primer, containing the underlined Xho I site, followed by 18 bp reverse and complementary to nucleotides 1822–1842 of the nucleotide sequence set forth in SEQ ID NO:1 has the following sequence: 5'-GCGCTCGAGTCAGGCATCCTTGCTCGGCCAG-3' (SEQ ID NO:16).

The PCR amplified DNA fragment is digested with Bgl II and Xho I. The vector, pcDNA3/Amp, is digested with BamH I and Xho I. The PCR amplified DNA fragment and the linearized vector are then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the hCRY2-encoding fragment.

For expression of recombinant hCRY2, COS cells are transfected with an expression vector, as described above, using DEAEDextran, as described, for instance, in Sambrook et al., *Molecular Cloning: a Laboratory Manual*, Cold Spring Laboratory Press, Cold Spring Harbor, N.Y. (1989). Cells are incubated under conditions for expression of hCRY2 by the vector.

Expression of the hCRY2-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

EXAMPLE 6(b)

Cloning and Expression in CHO Cells

The vector pC4 is used for the expression of hCRY2 protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofiolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., *J. Biol. Chem.* 253:1357–1370 (1978), Hamlin, J. L. and Ma, C., *Biochem. et Biophys. Acta*, 1097:107–143 (1990), Page, M. J. and Sydenham, M. A., *Biotechnology* 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are Bam H, Xbal, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express hCRY2 in a regulated way in mammalian cells (Gossen, M. and Bujard, H., *Proc. Natl. Acad. Sci. USA* 89: 5547–5551(1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamH I and Xba I and then dephosphorylated using calf intestinal phosphatase by procedures known in the art. The vector is then isolated from a 1% agarose gel.

The DNA sequence encoding the complete hCRY2 protein including its leader sequence is amplified using PCR oligonucleotide primers corresponding to the 5' and 3' sequences of the gene. The 5' primer has the sequence 5'-GCGAGATCTCCGCCATCATGGCGGCAACTGTGG-CAAC-3' (SEQ ID NO:14) containing the underlined Bgl II restriction enzyme site followed by an efficient signal for initiation of translation in eukaryotes, as described by Kozak, M, *J. Mol. Biol.* 196:947–950 (1987), and 22 bases corresponding to nucleotides −2 to 20 of SEQ ID NO:1. The 3' primer has the sequence 5'-GCGTCTAGATCAGG-CATCCTTGCTCGG-3' (SEQ ID NO:15), containing the underlined Xba I restriction site followed by a stop codon and 18 nucleotides reverse and complementary to nucleotide 1825–1842 in the sequence set forth in SEQ ID NO:1.

The amplified fragment is digested with the endonucleases Bgl II and Xba I and is then purified again on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofection (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/mil G418. After 2 days, the cells are trypsinized and seeded in hybridoma cloning plates (Greiner, Germany) in alpha minus MEM supplemented with 10, 25, or 50 ng/ml of methothrexate plus 1 mg/ml G418. After about 10–14 days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 m 20 mM). The same procedure is repeated until clones are obtained which grow at a concentration of 100–200 µM. Expression of the desired gene product is analyzed, for instance, by SDS-PAGE and Western blot or by reverse phase HPLC analysis.

EXAMPLE 7

Tissue Distribution of hCRY2 mRNA Expression

Northern blot analysis was carried out to examine hCRY2 gene expression in human tissues, using methods described by, among others, Sambrook et al., cited above. A cDNA probe containing the entire nucleotide sequence of the hCRY2 protein (SEQ ID NO:1) was labeled with $^{32}$P using the Rediprime™ DNA labeling system (Amersham Life Science, Arlington, Ill.), according to manufacturer's instructions. After labeling, the probe was purified using a CHROMA SPIN- 100™ column (Clontech Laboratories, Inc.), according to manufacturer's protocol number PT1200-1. The purified labeled probe was then used to examine various human tissues for hCRY2 mRNA.

Multiple Tissue Northern (MTN) blots containing various human tissues were obtained from Clontech and were examined with the labeled probe using ExpressHyb™ hybridization solution (Clontech) according to manufacturer's protocol number PT1190-1. Following hybridization and washing, the blots were mounted and exposed to film at −70° C. overnight, and films developed according to standard procedures.

Multiple, stronger signals, ranging size from about 1.4 to greater than about 9.5 kB, were detected in lanes corresponding to RNA from heart, brain, skeletal muscle, and pancreas. Weaker signals, ranging in size from about 1.4 to about 4 kb were detected in lanes corresponding to lung and kidney.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polypeptide comprising amino acids 191 to 571 in SEQ ID NO:2.

2. The isolated polypeptide of claim 1, comprising amino acids 1 to 571 of SEQ ID NO:2.

3. The isolated polypeptide of claim 2, comprising amino acids −21 to 571 of SEQ ID NO:2.

4. The isolated polypeptide of claim 3, comprising amino acids −22 to 571 of SEQ ID NO:2.

5. An isolated polypeptide comprising amino acids 1 to 492 NO:2.

6. The isolated polypeptide of claim 5, further comprising a heterologous polypeptide.

7. The isolated polypeptide of claim 5, which is produced by or contained in a recombinant host cell.

8. The isolated polypeptide of claim 7, wherein said recombinant host cell is mammalian.

9. An isolated polypeptide comprising the mature polypeptide having the amino acid sequence encoded by the cDNA clone contained in ATCC Deposit No. 97769.

10. The isolated polypeptide of claim 9, comprising the complete amino acid sequence encoded by the cDNA clone contained in ATCC Deposit No. 97769.

11. The isolated polypeptide of claim 9, further comprising a heterologous polypeptide.

12. The isolated polypeptide of claim 9, which is produced by or contained in a recombinant host cell.

13. The isolated polypeptide of claim 12, wherein said recombinant host cell is mammalian.

* * * * *

UNITED STATES PATENT AND TRADEMARK OFFICE
CERTIFICATE OF CORRECTION

PATENT NO. : 6,569,994 B1
DATED : May 27, 2003
INVENTOR(S) : Wei et al.

It is certified that error appears in the above-identified patent and that said Letters Patent is hereby corrected as shown below:

Title page,
Item [56], References Cited, OTHER PUBLICATIONS, "NCBI Entrez" reference, change "221657" to -- Z21657 --;
Item [57], ABSTRACT,
Line 1, change "blue-fight" to -- blue-light --;

Column 59,
Line 38, insert -- SEQ ID -- before "NO:2."

Signed and Sealed this

Twenty-third Day of November, 2004

JON W. DUDAS
*Director of the United States Patent and Trademark Office*

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 4185 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 51..1829

(ix) FEATURE:
      (A) NAME/KEY: mat_peptide
      (B) LOCATION: 117..1829

(ix) FEATURE:
      (A) NAME/KEY: sig_peptide
      (B) LOCATION: 51..116

(xi) SEQUENCE DESCRIPTION: SEQ ID NO:1:

```
GGCCACGCGT CGACTAGTAC GGGGGGGGGG GGGGGGCATT CTGGACAGTC ATG GCG        56
                                                       Met Ala
                                                       -22

GCA ACT GTG GCA ACG GCG GCA GCT GTG GCC CCG GCG CCA GCG CCC GGC      104
Ala Thr Val Ala Thr Ala Ala Ala Val Ala Pro Ala Pro Ala Pro Gly
-20                 -15                 -10                  -5

ACG GAC AGC GCC TCT TCG GTG CAC TGG TTC CGC AAA GGG CTG CGA CTC      152
```

-continued

```
Thr Asp Ser Ala Ser Ser Val His Trp Phe Arg Lys Gly Leu Arg Leu
              1               5                      10

CAC GAC AAC CCG GCG TTG CTG GCG GCC GTG CGC GGG GCG CGC TGC GTG          200
His Asp Asn Pro Ala Leu Leu Ala Ala Val Arg Gly Ala Arg Cys Val
            15                  20                  25

CGC TGC GTT TAC ATT CTC GAC CCG TGG TTC GCG GCC TCC TCC TCA GTC          248
Arg Cys Val Tyr Ile Leu Asp Pro Trp Phe Ala Ala Ser Ser Ser Val
        30                  35                  40

GGG ATC AAC CGA TGG AGG TTC CTA CTT CAG TCT CTG GAA GAT TTG GAC          296
Gly Ile Asn Arg Trp Arg Phe Leu Leu Gln Ser Leu Glu Asp Leu Asp
    45                  50                  55                  60

ACA AGT TTA AGG AAA CTG AAC TCC CGC CTG TTT GTA GTC CGG GGA CAG          344
Thr Ser Leu Arg Lys Leu Asn Ser Arg Leu Phe Val Val Arg Gly Gln
                65                  70                  75

CCA GCC GAC GTG TTC CCA AGG CTG TTC AAG GAA TGG GGA GTG ACC CGC          392
Pro Ala Asp Val Phe Pro Arg Leu Phe Lys Glu Trp Gly Val Thr Arg
            80                  85                  90

TTG ACC TTT GAA CAT GAC TCT GAA CCC TTT GGG AAA GAA CGG GAT GCA          440
Leu Thr Phe Glu His Asp Ser Glu Pro Phe Gly Lys Glu Arg Asp Ala
        95                  100                 105

GCC ATC ATG AAG ATG ACC AAG GAG GCT GGT GTG GAA GTA GTG ACG GAG          488
Ala Ile Met Lys Met Thr Lys Glu Ala Gly Val Glu Val Val Thr Glu
    110                 115                 120

AAT TCT CAT ACC CTC TAT GAC CTG GAC AGG ATC ATT GAG CTG AAT GGG          536
Asn Ser His Thr Leu Tyr Asp Leu Asp Arg Ile Ile Glu Leu Asn Gly
125                 130                 135                 140

CAG AAG CCA CCC CTT ACA TAC AAG CGC TTT CAG GCC ATC ATC AGC CGC          584
Gln Lys Pro Pro Leu Thr Tyr Lys Arg Phe Gln Ala Ile Ile Ser Arg
                145                 150                 155

ATG GAG CTG CCC AAG AAG CCA GTG GGC TTG GTG ACC AGC CGG CAG ATG          632
Met Glu Leu Pro Lys Lys Pro Val Gly Leu Val Thr Ser Arg Gln Met
            160                 165                 170

GAG AGC TGC AGG GCC GAG ATC CAG GAG AAC CAC GAC GAG ACC TAC GGC          680
Glu Ser Cys Arg Ala Glu Ile Gln Glu Asn His Asp Glu Thr Tyr Gly
        175                 180                 185

GTG CCC TCC CTG GAG GAG CTG GGG TTC CCC ACT GAA GGA CTT GGT CCA          728
Val Pro Ser Leu Glu Glu Leu Gly Phe Pro Thr Glu Gly Leu Gly Pro
    190                 195                 200

GCT GTC TGG CAG GGA GGA GAG ACA GAA GCT CTG GCC CGC CTG GAT AAG          776
Ala Val Trp Gln Gly Gly Glu Thr Glu Ala Leu Ala Arg Leu Asp Lys
205                 210                 215                 220

CAC TTG GAA CGG AAG GCC TGG GTT GCC AAC TAT GAG AGA CCC CGA ATG          824
His Leu Glu Arg Lys Ala Trp Val Ala Asn Tyr Glu Arg Pro Arg Met
                225                 230                 235

AAC GCC AAC TCC CTC CTG GCC AGC CCC ACA GGC CTC AGC CCC TAC CTG          872
Asn Ala Asn Ser Leu Leu Ala Ser Pro Thr Gly Leu Ser Pro Tyr Leu
            240                 245                 250

CGC TTT GGT TGT CTC TCC TGC CGC CTC TTC TAC TAC CGC CTG TGG GAC          920
Arg Phe Gly Cys Leu Ser Cys Arg Leu Phe Tyr Tyr Arg Leu Trp Asp
        255                 260                 265

CTG TAT AAA AAG GTG AAG CGG AAC AGC ACA CCT CCC CTC TCC CTA TTT          968
Leu Tyr Lys Lys Val Lys Arg Asn Ser Thr Pro Pro Leu Ser Leu Phe
    270                 275                 280

GGG CAA CTC CTA TGG CGA GAG TTC TTC TAC ACG GCA GCT ACC AAC AAC         1016
Gly Gln Leu Leu Trp Arg Glu Phe Phe Tyr Thr Ala Ala Thr Asn Asn
285                 290                 295                 300

CCC AGG TTT GAC CGC ATG GAG GGG AAC CCC ATC TGC ATC CAG ATC CCC         1064
Pro Arg Phe Asp Arg Met Glu Gly Asn Pro Ile Cys Ile Gln Ile Pro
                305                 310                 315
```

```
TGG GAC CGC AAT CCT GAG GCC CTG GCC AAG TGG GCT GAG GGC AAG ACA        1112
Trp Asp Arg Asn Pro Glu Ala Leu Ala Lys Trp Ala Glu Gly Lys Thr
            320                 325                 330

GGC TTC CCT TGG ATT GAT GCC ATC ATG ACC CAA CTG AGG CAG GAG GGC        1160
Gly Phe Pro Trp Ile Asp Ala Ile Met Thr Gln Leu Arg Gln Glu Gly
            335                 340                 345

TGG ATC CAC CAC CTG GCC CGG CAT GCC GTG GCC TGC TTC CTG ACC CGC        1208
Trp Ile His His Leu Ala Arg His Ala Val Ala Cys Phe Leu Thr Arg
350                 355                 360

GGG GAC CTC TGG GTC AGC TGG GAG AGC GGG GTC CGG GTA TTT GAT GAG        1256
Gly Asp Leu Trp Val Ser Trp Glu Ser Gly Val Arg Val Phe Asp Glu
365                 370                 375                 380

CTG CTC CTG GAT GCA GAT TTC AGC GTG AAC GCA GGC AGC TGG ATG TGG        1304
Leu Leu Leu Asp Ala Asp Phe Ser Val Asn Ala Gly Ser Trp Met Trp
                385                 390                 395

CTG TCC TGC AGT GCT TTC TTC CAG CAG TTC TTC CAC TGC TAC TGC CCT        1352
Leu Ser Cys Ser Ala Phe Phe Gln Gln Phe Phe His Cys Tyr Cys Pro
                400                 405                 410

GTG GGC TTT GGC CGT CGC ACG GAC CCC AGT GGG GAC TAC ATC AGG CGA        1400
Val Gly Phe Gly Arg Arg Thr Asp Pro Ser Gly Asp Tyr Ile Arg Arg
            415                 420                 425

TAC CTG CCC AAA TTG AAA GCG TTC CCC TCT CGA TAC ATC TAT GAG CCC        1448
Tyr Leu Pro Lys Leu Lys Ala Phe Pro Ser Arg Tyr Ile Tyr Glu Pro
    430                 435                 440

TGG AAT GCC CCA GAG TCA ATT CAG AAG GCA GCC AAG TGC ATC ATT GGT        1496
Trp Asn Ala Pro Glu Ser Ile Gln Lys Ala Ala Lys Cys Ile Ile Gly
445                 450                 455                 460

GTG GAC TAC CCA CGG CCC ATC GTC AAC CAT GCC GAG ACC AGC CGG CTT        1544
Val Asp Tyr Pro Arg Pro Ile Val Asn His Ala Glu Thr Ser Arg Leu
                465                 470                 475

AAC ATT GAA CGA ATG AAG CAG ATT TAC CAG CAG CTT TCG CGC TAC CGG        1592
Asn Ile Glu Arg Met Lys Gln Ile Tyr Gln Gln Leu Ser Arg Tyr Arg
                480                 485                 490

GGA CTC TGT CTA CTG GCA TCT GTC CCT TCC TGT GTG GAA GAC CTC AGT        1640
Gly Leu Cys Leu Leu Ala Ser Val Pro Ser Cys Val Glu Asp Leu Ser
            495                 500                 505

CAC CCT GTG GCA GAG CCC AGC TCG AGC CAG GCT GGC AGC ATG AGC AGT        1688
His Pro Val Ala Glu Pro Ser Ser Ser Gln Ala Gly Ser Met Ser Ser
510                 515                 520

GCA GGC CCA AGA CCA CTA CCC AGT GGC CCA GCA TCC CCC AAA CGC AAG        1736
Ala Gly Pro Arg Pro Leu Pro Ser Gly Pro Ala Ser Pro Lys Arg Lys
525                 530                 535                 540

CTG GAA GCA GCC GAG GAA CCA CCT GGT GAA GAA CTC AGC AAA CGG GCC        1784
Leu Glu Ala Ala Glu Glu Pro Pro Gly Glu Glu Leu Ser Lys Arg Ala
                545                 550                 555

CGG GTG GCA GAG TTG CCA ACC CCA GAG CTG CCG AGC AAG GAT GCC            1829
Arg Val Ala Glu Leu Pro Thr Pro Glu Leu Pro Ser Lys Asp Ala
            560                 565                 570

TGAGACTGCA GAGCCCTTGC TCCGTGAGCA AAGCCTGGGT GCCCAAGCAG CCACCGCAGC      1889

AGCAGAGTAC AACCTGCAGA GAAGCTGATC ACCGGGCAGA GATAGAGCGA GCATGTGTGT      1949

GTGTGTGCGC GTGTGCAGAG GAGGGAGTGG TGTGCCTGTT TGTGTGTGCA TGCATCTGTT      2009

GACACTCATG ATTCTGAATG TTGCCTGGGC TGGGGGAGTA CCTGTAGCAC GCCAGTGCTG      2069

TTTCCCGGCC TCCAGACACA AGGCTCGAGG TTATGGCAGT GACTTTCAGC TGAGACCTGT      2129

TCCTGCAAGC CAGCTGCCTT GTCTGAACAG AACGTAGTGG TAGGACCCTA GCTGGGATTC      2189

TGGCATCTGC CTCCCTAGAC CTCCTTCCCT CCCTCCTCAC GTCAGGCTGT GGAGCAGGAG      2249

CACAGCAGTT CTGGCTGTTG TCCAAAGCAT GGGATTCTGG AGGCAGCCAG AGCCCTGCTG      2309
```

-continued

```
AGTTCCTGCT TTCTGACCTG GAGGCTGAGC AGGCCGGAGT GGATGGATGC TGTCCAGACG    2369

TAGCCACCTG GCCTCTGTTT CTTATTTTAA AATTCTCTGC TACTGGGCTC AGTCCCAGGC    2429

CCTTCCTTGG GCTTCTGGGA CTGAGCATGA GGCCATAGAC AGATCTAAAA AGTTTCCACC    2489

ACCCTACAGA AGTACACACA GATACCTGAC TGGTGTGGGG TATGCCTGGT ACTGTAATAG    2549

GAGCCTAAGA CAGCACACCT ACCTTTTCAG GATTTAGAAC CTAAAATTAG AAAGAGAATC    2609

CCAGCTGTCA TTGTTCCTTC CCCAGAAGCT AAGAGCCAGC CTCAGAGCCT ACCCAGGAGC    2669

TGTGAAGGGG CAAGGGTCAA ACTGACTCAC TCTACCAGGA GGAGACCAGG TTGCAGTGGC    2729

GTAAGGCCCC CTGGTTTCTC TGGCCACACT CCAAGGCACC ACAGTGCTGC CAGTGAGGAC    2789

AGCTGACACC CAGCCAGGGA AACCATTCTA GTCTTTATTC TGTTGGCTTC CAGGGCCTGT    2849

CCTGAACTTG TCAGCATCCA GACTGCCATG TCAGCTATCC CAGTAGCTGA GCTCCAAGGA    2909

CTCAGGCAGA GGGACTCAGG GATGGGACT GCCAGGGCA GTTGGCAAAA GTCCAAGTAG    2969

AGATTACACC CAGAACACCA TTCCTTCCAG GAGCAGTAGG TGGGAGGTTT GACCCAGAGA    3029

AGCCAATCCT TGCATTCCAG GAGTGGCCTG TGCCTCCCAC CTCTTCCTTC CCACTGCCAA    3089

AGGCCTGTGT TGAGAAAGAT GTCATGCAAA AGGACGACGG TGGCCAACTA AAGCAAGTCT    3149

TCCTACCACC CTGTGGCCTG CACTTGAGCC ACAAAGTGTG TGTGTGTGTG TGCGTGTGTG    3209

GTAAGTGTGT GTGTGTGTGG CTATGAGGCT GATTCCTGTT TGGATTTTTG TCCTCACGTG    3269

TATCATTAAG CTGGCCTTTG GGCCTTTTCC TTTCTACCTC CCCTGTGACC TTTCCTAGCC    3329

TCAGATCTGT TAATTCTTTT GGCCCCAGCC CTGTCCCTCA CTGTCCTCTG TCCTTGGACC    3389

AGAACCCTGG GGTCAGACCC ATCTCCTGTA GCTGTCCATC ACACTGACAG GCTTCTTCCT    3449

GAGATATCCT CAGGTTTTCT CAGCCAGAGA GCTGCCTTTA GAGTCCAACT GTTGTACGTA    3509

TGTCACCTTC ACTAGAAATG TCCCATCATC GTGGGAGGGG AGCAGGGCAC AGGGGATGGT    3569

GTGCATTCAG AGCATTGGGT TGGGGGCTTC CCTGTTCCCT CAGCCCCAGT CGAGAGGAAA    3629

GAGAATCGGG CCACTGCCAG AAAGAGAGTC AAGCAAACCT GGAAGGGCAA ATCTGAGAGT    3689

GGGAAGGCCA AAGGCCGAGG CCCAGATTTA GTATTCACTA GCAGCGCCTT CGGGTAGCAG    3749

GATGATTCCT TTTCCTGCCT GTCTGCTGCT GGCTCTCTTC CCTAAGGTAC AGGTTGGCAG    3809

GACCACCTCC GCCTACTTCT CCACCATCCC TAGCATGCCA GCCCGTTCCC AGATCAACCT    3869

GCCAGTGGAG TCAGGCAGTG CACTCCTGGA GCCAAGAGGG AAGGGCAGGG TAGAGAGGGT    3929

ATGTCCAGTA GCCTGGAGCT CCATGGTGGC TTCATGCCTC CCTTCTCCCA GCTCAGGTGG    3989

CCCTGAGGGC TCCCTCGGAA CAGTGCCTCA AATCCTGACC CAAGGGCCAG CATGGGGAAG    4049

AGATGGTTGC AGGCAAAATG CACTTTATAG AGATTTTCTA TTGCTGGGAA GGTGTGTTTC    4109

TCCCACAATT TGTTTGTGAA TATTCACTTG TTTTATAAAT GTCTGACCTG TCTTGAGTAA    4169

AAAAAAAAAA AAAAAA                                                    4185
```

(2) INFORMATION FOR SEQ ID NO:2:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ala Thr Val Ala Thr Ala Ala Ala Val Ala Pro Ala Pro Ala
-22     -20                 -15                 -10
```

-continued

```
Pro Gly Thr Asp Ser Ala Ser Ser Val His Trp Phe Arg Lys Gly Leu
 -5              1                   5                      10

Arg Leu His Asp Asn Pro Ala Leu Leu Ala Ala Val Arg Gly Ala Arg
             15                  20                  25

Cys Val Arg Cys Val Tyr Ile Leu Asp Pro Trp Phe Ala Ala Ser Ser
             30                  35                  40

Ser Val Gly Ile Asn Arg Trp Arg Phe Leu Leu Gln Ser Leu Glu Asp
             45                  50                  55

Leu Asp Thr Ser Leu Arg Lys Leu Asn Ser Arg Leu Phe Val Val Arg
         60                  65                  70

Gly Gln Pro Ala Asp Val Phe Pro Arg Leu Phe Lys Glu Trp Gly Val
 75                  80                  85                  90

Thr Arg Leu Thr Phe Glu His Asp Ser Glu Pro Phe Gly Lys Glu Arg
             95                  100                 105

Asp Ala Ala Ile Met Lys Met Thr Lys Glu Ala Gly Val Glu Val Val
             110                 115                 120

Thr Glu Asn Ser His Thr Leu Tyr Asp Leu Asp Arg Ile Ile Glu Leu
             125                 130                 135

Asn Gly Gln Lys Pro Pro Leu Thr Tyr Lys Arg Phe Gln Ala Ile Ile
     140                 145                 150

Ser Arg Met Glu Leu Pro Lys Lys Pro Val Gly Leu Val Thr Ser Arg
155                 160                 165                 170

Gln Met Glu Ser Cys Arg Ala Glu Ile Gln Glu Asn His Asp Glu Thr
                 175                 180                 185

Tyr Gly Val Pro Ser Leu Glu Glu Leu Gly Phe Pro Thr Glu Gly Leu
             190                 195                 200

Gly Pro Ala Val Trp Gln Gly Gly Glu Thr Glu Ala Leu Ala Arg Leu
         205                 210                 215

Asp Lys His Leu Glu Arg Lys Ala Trp Val Ala Asn Tyr Glu Arg Pro
     220                 225                 230

Arg Met Asn Ala Asn Ser Leu Leu Ala Ser Pro Thr Gly Leu Ser Pro
235                 240                 245                 250

Tyr Leu Arg Phe Gly Cys Leu Ser Cys Arg Leu Phe Tyr Tyr Arg Leu
                 255                 260                 265

Trp Asp Leu Tyr Lys Lys Val Lys Arg Asn Ser Thr Pro Pro Leu Ser
             270                 275                 280

Leu Phe Gly Gln Leu Leu Trp Arg Glu Phe Phe Tyr Thr Ala Ala Thr
         285                 290                 295

Asn Asn Pro Arg Phe Asp Arg Met Glu Gly Asn Pro Ile Cys Ile Gln
     300                 305                 310

Ile Pro Trp Asp Arg Asn Pro Glu Ala Leu Ala Lys Trp Ala Glu Gly
315                 320                 325                 330

Lys Thr Gly Phe Pro Trp Ile Asp Ala Ile Met Thr Gln Leu Arg Gln
                 335                 340                 345

Glu Gly Trp Ile His His Leu Ala Arg His Ala Val Ala Cys Phe Leu
             350                 355                 360

Thr Arg Gly Asp Leu Trp Val Ser Trp Glu Ser Gly Val Arg Val Phe
         365                 370                 375

Asp Glu Leu Leu Leu Asp Ala Asp Phe Ser Val Asn Ala Gly Ser Trp
     380                 385                 390

Met Trp Leu Ser Cys Ser Ala Phe Phe Gln Phe His Cys Tyr
395                 400                 405                 410
```

```
Cys Pro Val Gly Phe Gly Arg Arg Thr Asp Pro Ser Gly Asp Tyr Ile
            415                 420                 425

Arg Arg Tyr Leu Pro Lys Leu Lys Ala Phe Pro Ser Arg Tyr Ile Tyr
            430                 435                 440

Glu Pro Trp Asn Ala Pro Glu Ser Ile Gln Lys Ala Ala Lys Cys Ile
            445                 450                 455

Ile Gly Val Asp Tyr Pro Arg Pro Ile Val Asn His Ala Glu Thr Ser
            460                 465                 470

Arg Leu Asn Ile Glu Arg Met Lys Gln Ile Tyr Gln Gln Leu Ser Arg
475                 480                 485                 490

Tyr Arg Gly Leu Cys Leu Leu Ala Ser Val Pro Ser Cys Val Glu Asp
            495                 500                 505

Leu Ser His Pro Val Ala Glu Pro Ser Ser Gln Ala Gly Ser Met
            510                 515                 520

Ser Ser Ala Gly Pro Arg Pro Leu Pro Ser Gly Pro Ala Ser Pro Lys
            525                 530                 535

Arg Lys Leu Glu Ala Ala Glu Glu Pro Pro Gly Glu Glu Leu Ser Lys
            540                 545                 550

Arg Ala Arg Val Ala Glu Leu Pro Thr Pro Glu Leu Pro Ser Lys Asp
555                 560                 565                 570

Ala
```

(2) INFORMATION FOR SEQ ID NO:3:

(i) SEQUENCE CHARACTERISTICS:
        (A) LENGTH: 586 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:3:

```
Met Gly Val Asn Ala Val His Trp Phe Arg Lys Gly Leu Arg Leu His
1               5                   10                  15

Asp Asn Pro Ala Leu Lys Glu Cys Ile Gln Gly Ala Asp Thr Ile Arg
            20                  25                  30

Cys Val Tyr Ile Leu Asp Pro Trp Phe Ala Gly Ser Ser Asn Val Gly
            35                  40                  45

Ile Asn Arg Trp Arg Phe Leu Leu Gln Cys Leu Glu Asp Leu Asp Ala
            50                  55                  60

Asn Leu Arg Lys Leu Asn Ser Arg Leu Phe Val Ile Arg Gly Gln Pro
65                  70                  75                  80

Ala Asp Val Phe Pro Arg Leu Phe Lys Glu Trp Asn Ile Thr Lys Leu
            85                  90                  95

Ser Ile Glu Tyr Asp Ser Glu Pro Phe Gly Lys Glu Arg Asp Ala Ala
            100                 105                 110

Ile Lys Lys Leu Ala Thr Glu Ala Gly Val Glu Val Ile Val Arg Ile
            115                 120                 125

Ser His Thr Leu Tyr Asp Leu Asp Lys Ile Ile Glu Leu Asn Gly Gly
            130                 135                 140

Gln Pro Pro Leu Thr Tyr Lys Arg Phe Gln Thr Leu Ile Ser Lys Met
145                 150                 155                 160

Glu Pro Leu Glu Ile Pro Val Glu Thr Ile Thr Ser Glu Val Ile Glu
            165                 170                 175

Lys Cys Thr Thr Pro Leu Ser Asp Asp His Asp Glu Lys Tyr Gly Val
```

```
              180                 185                 190
Pro Ser Leu Glu Glu Leu Gly Phe Asp Thr Asp Gly Leu Ser Ser Ala
            195                 200                 205
Val Trp Pro Gly Gly Glu Thr Glu Ala Leu Thr Arg Leu Glu Arg His
210                 215                 220
Leu Glu Arg Lys Ala Trp Val Ala Asn Phe Glu Arg Pro Arg Met Asn
225                 230                 235                 240
Ala Asn Ser Leu Leu Ala Ser Pro Thr Gly Leu Ser Pro Tyr Ile Arg
                245                 250                 255
Phe Gly Cys Leu Ser Cys Arg Leu Phe Tyr Phe Lys Leu Thr Asp Leu
                260                 265                 270
Tyr Lys Lys Val Lys Lys Asn Ser Ser Pro Pro Leu Ser Leu Tyr Gly
                275                 280                 285
Gln Leu Leu Trp Arg Glu Phe Phe Tyr Thr Ala Ala Thr Asn Asn Pro
            290                 295                 300
Arg Phe Asp Lys Met Glu Gly Asn Pro Ile Cys Val Gln Ile Pro Trp
305                 310                 315                 320
Asp Lys Asn Pro Glu Ala Leu Ala Lys Trp Ala Glu Gly Arg Thr Gly
                325                 330                 335
Phe Pro Trp Ile Asp Ala Ile Met Thr Gln Leu Arg Gln Glu Gly Trp
                340                 345                 350
Ile His His Leu Ala Arg His Ala Val Ala Cys Phe Leu Thr Arg Gly
                355                 360                 365
Asp Leu Trp Ile Ser Trp Glu Glu Gly Met Lys Val Phe Glu Glu Leu
            370                 375                 380
Ile Leu Asp Ala Asp Trp Ser Ile Asn Ala Gly Ser Trp Met Trp Leu
385                 390                 395                 400
Ser Cys Ser Ser Phe Phe Gln Gln Phe Phe His Cys Tyr Cys Pro Val
                405                 410                 415
Gly Phe Gly Arg Arg Thr Asp Pro Asn Gly Asp Tyr Ile Arg Arg Tyr
                420                 425                 430
Leu Pro Val Leu Arg Gly Phe Pro Ala Lys Tyr Ile Tyr Asp Pro Trp
                435                 440                 445
Asn Ala Pro Glu Gly Ile Gln Lys Val Ala Lys Cys Leu Ile Gly Val
450                 455                 460
Asn Tyr Pro Lys Pro Met Val Asn His Ala Glu Ala Ser Arg Leu Asn
465                 470                 475                 480
Ile Glu Arg Met Lys Gln Ile Tyr Gln Gln Leu Ser Arg Tyr Arg Gly
                485                 490                 495
Leu Gly Leu Leu Ala Ser Val Pro Ser Asn Pro Asn Gly Asn Gly Gly
                500                 505                 510
Phe Met Gly Tyr Ser Ala Glu Asn Ile Pro Gly Cys Ser Ser Ser Gly
                515                 520                 525
Ser Cys Ser Gln Gly Ser Gly Ile Leu His Tyr Ala His Gly Asp Ser
                530                 535                 540
Gln Gln Thr His Leu Leu Lys Gln Gly Arg Ser Ser Met Gly Thr Gly
545                 550                 555                 560
Leu Ser Gly Gly Lys Arg Pro Ser Gln Glu Glu Asp Thr Gln Ser Ile
                565                 570                 575
Gly Pro Lys Val Gln Arg Gln Ser Thr Asn
                580                 585
```

(2) INFORMATION FOR SEQ ID NO:4:

(i) SEQUENCE CHARACTERISTICS:
    (A) LENGTH: 472 amino acids
    (B) TYPE: amino acid
    (C) STRANDEDNESS: Not Relevant
    (D) TOPOLOGY: linear (ii) MOLECULE TYPE: protein (xi) SEQUENCE DESCRIPTION: SEQ ID NO:4:

```
Met Thr Thr His Leu Val Trp Phe Arg Gln Asp Leu Arg Leu His Asp
1               5                   10                  15

Asn Leu Ala Ile Ala Ala Cys Arg Asn Ser Ser Ala Arg Val Leu
            20                  25                  30

Ala Leu Tyr Ile Ala Thr Pro Arg Gln Trp Ala Thr His Asn Met Ser
            35                  40                  45

Pro Arg Gln Ala Glu Leu Ile Asn Ala Gln Ile Asn Gly Leu Gln Ile
50                      55                  60

Ala Leu Ala Glu Lys Gly Ile Pro Leu Leu Phe Arg Glu Val Asp Asp
65                  70                  75                  80

Phe Val Ala Ser Val Glu Ile Val Lys Gln Val Cys Ala Glu Asn Ser
                85                  90                  95

Val Thr His Leu Phe Tyr Asn Tyr Gln Tyr Glu Val Asn Glu Arg Ala
                100                 105                 110

Arg Asp Val Glu Val Glu Arg Ala Leu Arg Asn Val Val Cys Glu Gly
            115                 120                 125

Phe Asp Asp Ser Val Ile Leu Pro Pro Gly Ala Val Met Thr Gly Asn
130                 135                 140

His Glu Met Tyr Lys Val Phe Thr Pro Phe Lys Asn Ala Trp Leu Lys
145                 150                 155                 160

Arg Leu Arg Glu Gly Met Pro Glu Cys Val Ala Ala Pro Lys Val Arg
                165                 170                 175

Ser Ser Gly Ser Ile Glu Pro Ser Pro Ser Ile Thr Leu Asn Tyr Pro
                180                 185                 190

Arg Gln Ser Phe Asp Thr Ala His Phe Pro Val Glu Glu Lys Ala Ala
            195                 200                 205

Ile Ala Gln Leu Arg Gln Phe Cys Gln Asn Gly Ala Gly Glu Tyr Glu
210                 215                 220

Gln Gln Arg Asp Phe Pro Ala Val Glu Gly Thr Ser Arg Leu Ser Ala
225                 230                 235                 240

Ser Ile Ala Thr Gly Gly Leu Ser Pro Arg Gln Cys Leu His Arg Leu
                245                 250                 255

Leu Ala Glu Gln Pro Gln Ala Leu Asp Gly Gly Ala Gly Ser Val Trp
                260                 265                 270

Leu Asn Glu Leu Ile Trp Arg Glu Phe Tyr Arg His Leu Ile Thr Tyr
            275                 280                 285

His Pro Ser Leu Cys Lys His Arg Pro Phe Ile Ala Trp Thr Asp Arg
290                 295                 300

Val Gln Trp Gln Ser Asn Pro Ala His Leu Gln Ala Trp Gln Glu Gly
305                 310                 315                 320

Lys Thr Gly Tyr Pro Ile Val Asp Ala Ala Met Arg Gln Leu Asn Ser
                325                 330                 335

Thr Gly Trp Met His Asn Arg Leu Arg Met Ile Thr Ala Ser Phe Leu
                340                 345                 350

Val Lys Asp Leu Leu Ile Asp Trp Arg Glu Gly Glu Arg Tyr Phe Met
            355                 360                 365
```

```
Ser Gln Ile Ile Asp Gly Asp Leu Ala Ala Asn Asn Gly Gly Trp Gln
    370                 375                 380

Trp Ala Ala Ser Thr Gly Thr Asp Ala Ala Pro Tyr Phe Arg Ile Phe
385                 390                 395                 400

Asn Pro Thr Thr Gln Gly Glu Lys Phe Asp His Glu Gly Glu Phe Ile
                405                 410                 415

Arg Gln Trp Leu Pro Glu Leu Arg Asp Val Pro Gly Lys Val Val His
                420                 425                 430

Glu Pro Trp Lys Trp Ala Gln Lys Ala Gly Val Thr Leu Asp Tyr Pro
            435                 440                 445

Gln Pro Ile Val Glu His Lys Glu Ala Arg Val Gln Thr Leu Ala Ala
        450                 455                 460

Tyr Glu Ala Ala Arg Lys Gly Lys
465                 470
```

(2) INFORMATION FOR SEQ ID NO:5:

(i) SEQUENCE CHARACTERISTICS:
        (A) LENGTH: 681 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

```
Met Ser Gly Ser Val Ser Gly Cys Gly Ser Gly Gly Cys Ser Ile Val
1               5                   10                  15

Trp Phe Arg Arg Asp Leu Arg Val Glu Asp Asn Pro Ala Ile Ala Ala
            20                  25                  30

Ala Val Arg Ala Gly Pro Val Ile Ala Leu Phe Val Trp Ala Pro Glu
        35                  40                  45

Glu Glu Gly His Tyr His Pro Gly Arg Val Ser Arg Trp Trp Leu Lys
    50                  55                  60

Asn Ser Leu Ala Gln Leu Asp Ser Ser Leu Arg Ser Leu Gly Thr Cys
65                  70                  75                  80

Leu Ile Thr Lys Arg Ser Thr Asp Ser Val Ala Ser Leu Leu Asp Val
                85                  90                  95

Val Lys Ser Thr Gly Ala Ser Gln Ile Phe Phe Asn His Leu Tyr Asp
            100                 105                 110

Pro Leu Ser Leu Val Arg Asp His Arg Ala Lys Asp Val Leu Thr Ala
        115                 120                 125

Gln Gly Ile Ala Val Arg Ser Phe Asn Ala Asp Leu Leu Tyr Glu Pro
    130                 135                 140

Trp Glu Val Thr Asp Glu Leu Gly Arg Pro Phe Ser Met Phe Ala Ala
145                 150                 155                 160

Phe Trp Glu Arg Cys Leu Ser Met Pro Tyr Asp Pro Glu Ser Pro Leu
                165                 170                 175

Leu Pro Pro Lys Lys Ile Ile Ser Gly Asp Val Ser Lys Cys Val Ala
            180                 185                 190

Asp Pro Leu Val Phe Glu Asp Ser Glu Lys Gly Ser Asn Ala Leu
        195                 200                 205

Leu Ala Arg Ala Trp Ser Pro Gly Trp Ser Asn Gly Asp Lys Ala Leu
    210                 215                 220

Thr Thr Phe Ile Asn Gly Pro Leu Leu Glu Tyr Ser Lys Asn Arg Arg
225                 230                 235                 240
```

-continued

```
Lys Ala Asp Ser Ala Thr Thr Ser Phe Leu Ser Pro His Leu His Phe
                245                 250                 255
Gly Glu Val Ser Val Arg Lys Val Phe His Leu Val Arg Ile Lys Gln
            260                 265                 270
Val Ala Trp Ala Asn Glu Gly Asn Glu Ala Gly Glu Ser Val Asn
        275                 280                 285
Leu Phe Leu Lys Ser Ile Gly Leu Arg Glu Tyr Ser Arg Tyr Ile Ser
    290                 295                 300
Phe Asn His Pro Tyr Ser His Glu Arg Pro Leu Leu Gly His Leu Lys
305                 310                 315                 320
Phe Phe Pro Trp Ala Val Asp Glu Asn Tyr Phe Lys Ala Trp Arg Gln
                325                 330                 335
Gly Arg Thr Gly Tyr Pro Leu Val Asp Ala Gly Met Arg Glu Leu Trp
            340                 345                 350
Ala Thr Leu Trp Leu His Asp Arg Ile Arg Val Val Ser Ser Phe
        355                 360                 365
Phe Val Lys Val Leu Gln Leu Pro Trp Arg Trp Gly Met Lys Tyr Phe
    370                 375                 380
Trp Asp Thr Leu Leu Asp Ala Asp Leu Glu Ser Asp Ala Leu Gly Trp
385                 390                 395                 400
Gln Tyr Ile Thr Gly Thr Leu Pro Asp Ser Arg Glu Phe Asp Arg Ile
                405                 410                 415
Asp Asn Pro Gln Phe Glu Gly Tyr Lys Phe Asp Pro Asn Gly Glu Tyr
            420                 425                 430
Val Arg Arg Trp Leu Pro Glu Leu Ser Arg Leu Pro Thr Asp Trp Ile
        435                 440                 445
His His Pro Trp Asn Ala Pro Glu Ser Val Leu Gln Ala Ala Gly Ile
    450                 455                 460
Glu Leu Gly Ser Asn Tyr Pro Leu Pro Ile Val Gly Leu Asp Glu Ala
465                 470                 475                 480
Lys Ala Arg Leu His Glu Ala Leu Ser Gln Met Trp Gln Leu Glu Ala
                485                 490                 495
Ala Ser Arg Ala Ala Ile Glu Asn Gly Ser Glu Glu Gly Leu Gly Asp
            500                 505                 510
Ser Ala Glu Val Glu Glu Ala Pro Ile Glu Phe Pro Arg Asp Ile Thr
        515                 520                 525
Met Glu Glu Thr Glu Pro Thr Arg Leu Asn Pro Asn Arg Arg Tyr Glu
    530                 535                 540
Asp Gln Met Val Pro Ser Ile Thr Ser Ser Leu Ile Arg Pro Glu Glu
545                 550                 555                 560
Asp Glu Glu Ser Ser Leu Asn Leu Arg Asn Ser Val Gly Asp Ser Arg
                565                 570                 575
Ala Glu Val Pro Arg Asn Met Val Asn Thr Asn Gln Ala Gln Gln Arg
            580                 585                 590
Arg Ala Glu Pro Ala Ser Asn Gln Val Thr Ala Met Ile Pro Glu Phe
        595                 600                 605
Asn Ile Arg Ile Val Ala Glu Ser Thr Glu Asp Ser Thr Ala Glu Ser
    610                 615                 620
Ser Ser Ser Gly Arg Arg Glu Arg Ser Gly Gly Ile Val Pro Glu Trp
625                 630                 635                 640
Ser Pro Gly Tyr Ser Glu Gln Phe Pro Ser Glu Glu Asn Arg Ile Gly
                645                 650                 655
```

```
Gly Gly Ser Thr Thr Ser Ser Tyr Leu Gln Asn His His Glu Ile Leu
            660                 665                 670

Asn Trp Arg Arg Leu Ser Gln Thr Gly
        675                 680
```

(2) INFORMATION FOR SEQ ID NO:6:

(i) SEQUENCE CHARACTERISTICS:
        (A) LENGTH: 540 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

```
Met Asp Ser Gln Arg Ser Thr Leu Val His Trp Phe Arg Lys Gly Leu
1               5                   10                  15

Arg Leu His Asp Asn Pro Ala Leu Ser His Ile Phe Thr Ala Ala Asn
            20                  25                  30

Ala Ala Pro Gly Lys Tyr Phe Val Arg Pro Ile Phe Ile Leu Asp Pro
        35                  40                  45

Gly Ile Leu Asp Trp Met Gln Val Gly Ala Asn Arg Trp Arg Phe Leu
50                  55                  60

Gln Gln Thr Leu Glu Asp Leu Asp Asn Gln Leu Arg Lys Leu Asn Ser
65                  70                  75                  80

Arg Leu Phe Val Val Arg Gly Lys Pro Ala Glu Val Phe Pro Arg Ile
            85                  90                  95

Phe Lys Ser Trp Arg Val Glu Met Leu Thr Phe Glu Thr Asp Ile Glu
            100                 105                 110

Pro Tyr Ser Val Thr Arg Asp Ala Ala Val Gln Lys Leu Ala Lys Ala
            115                 120                 125

Glu Gly Val Arg Val Glu Thr His Cys Ser His Thr Ile Tyr Asn Pro
        130                 135                 140

Glu Leu Val Lys Ala Lys Asn Leu Gly Lys Ala Pro Ile Thr Tyr Gln
145                 150                 155                 160

Lys Phe Leu Gly Ile Val Glu Gln Leu Lys Val Pro Lys Val Leu Gly
            165                 170                 175

Val Pro Glu Lys Leu Lys Lys Met Pro Thr Pro Lys Asp Glu Val
            180                 185                 190

Glu Gln Lys Asp Ser Ala Ala Tyr Asp Cys Pro Thr Ile Lys Gln Leu
            195                 200                 205

Val Lys Arg Pro Glu Glu Leu Gly Pro Asn Lys Phe Pro Gly Gly Glu
        210                 215                 220

Thr Glu Ala Leu Arg Arg Met Glu Glu Ser Leu Lys Asp Glu Ile Trp
225                 230                 235                 240

Val Ala Arg Phe Glu Lys Pro Asn Thr Ala Pro Asn Ser Leu Glu Pro
            245                 250                 255

Ser Thr Val Leu Ser Pro Tyr Leu Lys Phe Gly Cys Leu Ser Ala
            260                 265                 270

Arg Leu Phe Asn Gln Lys Leu Lys Glu Ile Ile Lys Arg Gln Pro Lys
            275                 280                 285

His Ser Gln Pro Pro Val Ser Leu Ile Gly Gln Leu Met Trp Arg Glu
        290                 295                 300

Phe Tyr Tyr Thr Val Ala Ala Ala Glu Pro Asn Phe Asp Arg Met Leu
305                 310                 315                 320
```

Gly Asn Val Tyr Cys Met Gln Ile Pro Trp Gln Glu His Pro Asp His
            325                 330                 335

Leu Glu Ala Trp Thr His Gly Arg Thr Gly Tyr Pro Phe Ile Asp Ala
            340                 345                 350

Ile Met Arg Gln Leu Arg Gln Glu Gly Trp Ile His His Leu Ala Arg
            355                 360                 365

His Ala Val Ala Cys Phe Leu Thr Arg Gly Asp Leu Trp Ile Ser Trp
            370                 375                 380

Glu Glu Gly Gln Arg Val Phe Glu Gln Leu Leu Leu Asp Gln Asp Trp
385                 390                 395                 400

Ala Leu Asn Ala Gly Asn Trp Met Trp Leu Ser Ala Ser Ala Phe Phe
            405                 410                 415

His Gln Tyr Phe Arg Val Tyr Ser Pro Val Ala Phe Gly Lys Lys Thr
            420                 425                 430

Asp Pro Gln Gly His Tyr Ile Arg Lys Tyr Val Pro Glu Leu Ser Lys
            435                 440                 445

Tyr Pro Ala Thr Cys Ile Tyr Glu Pro Trp Lys Ala Ser Leu Val Asp
            450                 455                 460

Gln Arg Ala Tyr Gly Cys Val Leu Gly Thr Asp Tyr Pro His Arg Ile
465                 470                 475                 480

Val Lys His Glu Val Val His Lys Glu Asn Ile Lys Arg Met Gly Ala
            485                 490                 495

Ala Tyr Lys Val Asn Arg Glu Val Arg Thr Gly Lys Glu Glu Glu Ser
            500                 505                 510

Ser Phe Glu Glu Lys Ser Glu Thr Ser Thr Ser Gly Lys Arg Lys Val
            515                 520                 525

Arg Arg Ala Thr Gly Ser Ala Pro Lys Arg Lys Arg
530                 535                 540

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GGGCTCTGCC ACAGGGTGAC TGAGGTC                                27

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AATACCCGGA CCCCGCTC                                          18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:9:

CAGGTCCCAC AGGCGGTA                                                         18

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CGCGAATTCC TCCCTGGAGG AGCTGGG                                               27

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCGAGATCTT CAGGCATCCT TGCTCGG                                               27

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GCGGATATCG CGGCAGCTGT GGCCCCG                                               27

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GCGAAGCTTT CAGGCATCCT TGCTCGG                                               27

(2) INFORMATION FOR SEQ ID NO:14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GCGAGATCTC CGCCATCATG GCGGCAACTG TGGCAAC                        37

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GCGTCTAGAT CAGGCATCCT TGCTCGG                                  27

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCGCTCGAGT CAGGCATCCT TGCTCGGCCA G                             31

(2) INFORMATION FOR SEQ ID NO:17:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

CTGCAGTGCT TCTTCCAGC AGTTCTTCCA CTGCTACTGC CCTGTGGGCT TTGGCCGTCG    60

CACGGACCCC AGTGGGGACT ACATCAGGCG ATACCTGCCC AAATTGAAAG CGTTCCCCTC   120

TCGATACATC TATGAGCCCT GGAATGCCCC AGAGTCAATT CAGAAGGCAG CCAAGTGCAT   180

CATTGGTGTG GACTACCCAC GGCCCATCGT CAACCATGCC GAGACCAGCC GGCTTAACAT   240

TGAACGAATG AAGCAGATTT ACCAGCAGCT TTCGCGCTAC CGGGGACTTT TGTCTAATGG   300

CATCTGTNCC TTCCTGTNTG GAAGACTCAG TCAA                              334

(2) INFORMATION FOR SEQ ID NO:18:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GCTTACATAC AAGCGCTTTC AGGCCATCAT CAGCCGCATG GAGCTGCCCA AGAAGCCAGT    60

GGGCTTGGTG ACCAGCCAGC AGATGGAGAG CTGCAGGGCC GAGGATCCAG AGAACCACG   120

ACGAGACCTA CGGCGTGCNC TCCCTGGTAG NAGCTGGGGT TCCCCACTGT AAGGACTTGG   180

TCNAGCTGTN TGGCCAGGAG GTAGAGACAG AAGCTCTGGC CCGCCTGGAT AAGCACTTNG   240

```
GAANGGAANG NCTGGGTTGC CAACTATGAG AGANCCCGAA TGAACGCCAA CTTCCCTCCT    300

GG                                                                   302

(2) INFORMATION FOR SEQ ID NO:19:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

AATTCGGCAN GAGGTGCCTT ATAGAGTCCA ACTGTTGTAC GTATGTNACC TTCACTAGAA     60

ATGTCCCATC ATCGTGGGAG GGGAGCAGGG CACAGGGGAT GGTGTGCATT TAGAGCATTG    120

GGTTNGGGGC TTCCCTGTTC CCTCAGCCCC AGTNGAGAGG NAANGAGAAT CGGGGCCACT    180

NNCAGAAAGA GAGTCAAGCA AACCTGGGNA GGGCAAATNT NTGGAGTGGG AAGGCCAAAG    240

GCCCGGGGCC CAGATTTAGT ATTNANTAGC AGCGCCTTCG GGGTAGCANG GTGGATTCCT    300

TTTCCTGNCT GTNTGNTGNT GGNTTCTTTT TCCCTNAGGT TANANGTTTG GCANGACCAA    360

CTTTCGGNNT AATTTTTTCC ANCANNCTTA GGCATGGCAN NCCNTTTNCC CNGTTCAACT    420

TNTCCAATGG GGGTTCAGGN NATTGCAATT CTTGGNGGCC AANNGGGGAG GGCNAGGTTA    480

GAGAGGGTAT TTNCC                                                    495

(2) INFORMATION FOR SEQ ID NO:20:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

AAAATTCTCT GCTACTGGNC TCAGTCCCAG GCCCTTCCTT GGGCTTNTGG GACTGAGCAT     60

GAGGCCATAG ACAGATCTAA AAAGTTTCCA CCACCCTACA GAAGTACACA CAGATACCTG    120

ACTGGTGTGG GGTATGCCTG GGTACTGTAA TAGGAGNNTA AGACAGCACA CCTACCTTTT    180

CAGGNNTTTA GGAACCTAAA AATTAGAAAG GGGAATTCCC AGCTGTCAAT TGNTCCTTCC    240

CCAGAAGCTA AGAGGCCAGC CTTCAGAGGC TACCCAGGGA GCTGTGAAGG GGCAAGGNGT    300

CAAACCTGAC TTCAATT                                                  317

(2) INFORMATION FOR SEQ ID NO:21:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CTGCAGTGCT TCTTCCAGC AGTTCTTCCA CTGCTACTGC CCTGTGGGCT TTGGCCGTCG      60

CACGGACCCC AGTGGGGACT ACATCAGGCG ATACCTGCCC AAATTGAAAG CGTTCCCCTC    120

TCGATACATC TATGAGCCCT GGAATGCCCC AGAGTCAATT CAGAAGGCAG CCAAGTGCAT    180
```

```
CATTGGTGTG GACTACCCAC GGCCCATCGT CAACCATGCC GAGACCAGCC GGCTTAACAT        240

TGAACGAATG AAGCAGATTT ACCAGCAGCT TTCGCGCTAC CGGGGACTTT TGTCTAATGG        300

CATCTGTNCC TTCCTGTNTG GAAGACTCAG TCAA                                   334

(2) INFORMATION FOR SEQ ID NO:22:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

CAGGAGGGCT GGTTCCACCA CCTGGCCCGG NATGCCGTGG CCTGCTTCCT GACCCGCGGG         60

GACCTNTGGN TCAGCTGGGA GAGCGGGGTC CGGGTATTTA ATGAGCTGCT CCTGGATGCA        120

GATTTAAGCG TGAACGCAGG CAGCTGGATG TGGCTGTCCT GCAGTGCTTT TTTCCAGCAG        180

TTNTTCCACT GCTACTGCCC TGTGGGTTTT                                        210
```